United States Patent
Chebib et al.

(10) Patent No.: US 6,962,907 B2
(45) Date of Patent: Nov. 8, 2005

(54) NEUROLOGICALLY-ACTIVE COMPOUNDS

(75) Inventors: Mary Chebib, Leichhardt (AU); Jane Hanrahan, Newtown (AU); Graham A. R. Johnston, Roseville (AU)

(73) Assignees: The University of Sydney, Sydney (AU); Polychip Pharmaceuticals Pty. Ltd., Toorak (AU)

( * ) Notice: Subject to any disclaimer, the term of this patent is extended or adjusted under 35 U.S.C. 154(b) by 0 days.

(21) Appl. No.: 10/496,904

(22) PCT Filed: Nov. 29, 2002

(86) PCT No.: PCT/AU02/01624

§ 371 (c)(1),
(2), (4) Date: Sep. 3, 2004

(87) PCT Pub. No.: WO03/045897

PCT Pub. Date: Jun. 5, 2003

(65) Prior Publication Data

US 2005/0004083 A1 Jan. 6, 2005

(30) Foreign Application Priority Data

Nov. 30, 2001 (AU) ............................................. PR 9203

(51) Int. Cl.[7] .......................... A61K 31/662; C07F 9/30
(52) U.S. Cl. ........................................ 514/114; 562/11
(58) Field of Search ............................. 562/11; 514/114

(56) References Cited

FOREIGN PATENT DOCUMENTS

WO    WO 98/58939    12/1998

OTHER PUBLICATIONS

Specification for Australian Provisional Patent Application No.: PO7501; filed Jun. 23, 1997; Title: Neurologically–Active Compounds.
Specification for Australian Provisional Patent Application No.: PP2985; filed Apr. 17, 1998; Title: Neurologically–Active Compounds.
Chebib, M., Vandenberg R.J., Froestl W. and Johnston G.A.R., Eur. J. Pharmacol., 1997 329, 223–229.
Chebib, M., Chemistry in Australia, Oct. 2001, 68(a) 19–21.
Chebib, M. and Johnston G.A.R., J. Med. Chem, 2000 ,43, 1427–1447.
Drew C.A., Johnson G.A.R., and Weatherby R.P. Neurosci. Let. 1984, 52, 317–321.
Feigenspan A. Wossle H. and Bormann J., Nature, 1993, 361, 159–162.
Froestl W., Mickel, S.J., von Sprecher, G., Diel. P.J., Hall, R.G., Maier, L., Strub, D., Melillo, V., Baumann, P.A., Bernasconi, R., Gentsch, C., Hauser, K., Jaekel, J., Karlsson, G., Klebs, K., Maitre, L., Marescaux, C., Pozza, M.F., Schmutz, M., Steinmann, M.W., Riezen, H., Vassout, A., Moudadori, C., Olpe, H–R., Waldmeier, P.C., and Bittiger, H., J. Mec. Chem., 1995, 38, 3313–3331.

Irwin, S. "Comprehensive Observational Assessment: 1a. A Systematic, Quantitiative Procedure for Assessing the Behavioural and Physiologic State of the Mouse," Psychopharmacologia, 1968, 13, 222–257.

Johnston, G.A.R., Curtis, D.R., Beart, P.M., Game, C.J.A., McCulloch, R.M. and Twitchin, B.J. Neurochem, 1975, 24, 157–160.

Johnston, G.A.R., Allan, R.D., Kennedy, S.M.E. and Twitchen, B., "GABA–Neurotransmitters", Alfred Benzon Symposium 12, Munksgaard, 1978, p 149–164.

Johnston, G.A.R. Pharmacol. Ther., 1996, 69, 173–198 ("Johnston, 1996a").

Johnston, G.A.R. Trends Pharmacol. Sci., 1996, 17, 319–323. ("Johnston, 1996b").

Kerr, D.I.B. and Ong, J. Pharmacol. Ther., 1995, 67, 187–246.

Murata, Y., Woodward, R.M., Miledi, R. and Overman, L.E. Bioorg. and Med. Chem. Lett., 1996, 6, 2073–2076.

Piers, E., Grierson, J.R., Lau, C.K. and Nagakura, I., Can. J. Chem. 1982, 60,210.

Qian, H. and Dowling, J.E., Nature 1993, 361, 162–164.

Ragozzino, D., Woodward, R.M., Murata, F., Eusebi, F., Overman, L.E. and Miledi, R. , Mol. Pharmacol., 1996, 50. 1024–1030.

Woodward, R.M., Polanzani, L. and Miledi, R. Mol. Pharmacol., 1993, 43, 609–625.

Primary Examiner—Fiona T. Powers
(74) Attorney, Agent, or Firm—Welsh & Katz, Ltd.

(57) ABSTRACT

The invention provides compounds of the formula II:

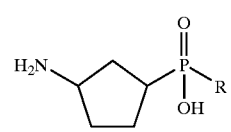

wherein R represents propyl, butyl, pentyl, neo-pentyl or cyclohexyl, and salts thereof. These compounds are selective GABA$_C$ receptor antagonists. The invention also provides a method of enhancing the cognitive activity of an animal and a method of stimulating memory capacity in an animal, comprising administering to the animal an effective amount of a compound of formula II or a pharmaceutically acceptable salt thereof.

17 Claims, 12 Drawing Sheets

GABA

TACA

CACA

CGP27492

3-APA

CGP35024

TPMPA

CGP36742

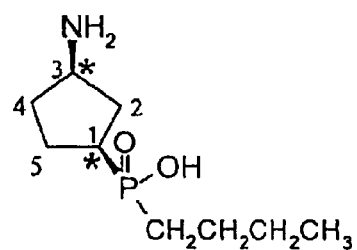
+
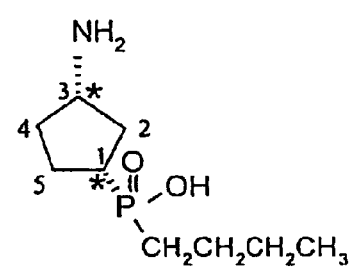
FIGURE 3
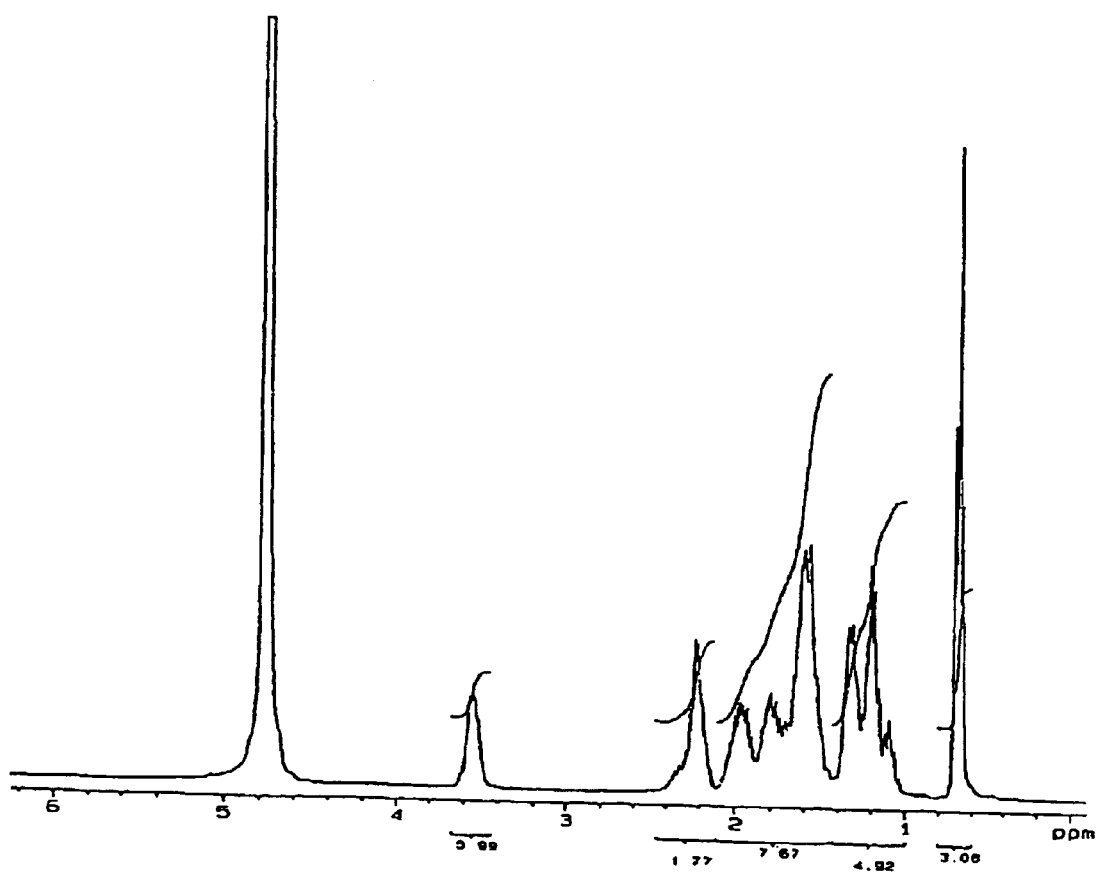

(a)

(b)

NEUROLOGICALLY-ACTIVE COMPOUNDS

TECHNICAL FIELD

This invention relates to compounds which are antagonists of $GABA_C$ receptors, and to methods of treatment using those compounds. In particular, the invention relates to methods of enhancing cognitive activity using the compounds.

BACKGROUND OF THE INVENTION

There are three major sub-types of GABA receptors in the central nervous system (CNS): $GABA_A$, $GABA_B$ and $GABA_C$ receptors. The pharmacology of $GABA_A$ and $GABA_B$ receptors has been extensively investigated. $GABA_C$ receptors are the most recently described sub-type of GABA receptors, and are therefore the least studied sub-type.

γ-Aminobutyric acid (GABA) is the main inhibitory neurotransmitter in the central nervous system (CNS) and activates the three major sub-types of GABA receptors in the central nervous system (CNS), the $GABA_A$, $GABA_B$ and $GABA_C$ receptors. $GABA_A$ receptors are ligand gated $Cl^-$ ion channels which are inhibited by the alkaloid bicuculline (Johnston, 1996a). $GABA_A$ receptors are heterooligomeric made up of α, β, γ, δ and θ subunits. $GABA_B$ receptors are transmembrane receptors coupled to second membrane messenger systems and $Ca^+$ and $K^+$ Channels via G-proteins. These receptors are not blocked by bicuculline, but are activated by (−)-baclophen and 3-aminopropylphosphinic acid (CGP27492) and blocked by saclofen (Kerr and Ong, 1995).

$GABA_C$ receptors (sometimes called $GABA_{NANB}$ or ρ receptors) were first proposed when a series of conformationally restricted GABA analogues, including cis-4-aminocrotonic acid (CACA), that had bicuculline insensitive depression actions on neuronal activity, showed no affinity for [$^3$H]baclofen binding sites in rat cerebellar membranes (Drew et al, 1984). $GABA_C$ receptors with similar pharmacology were first found in neurons in rat retina (Feigenspan et al, 1993) and white perch retina (Qian et al, 1993).

Three major sub-types of $GABA_C$ receptors are now known, namely ρ1, ρ2 and ρ3 (Chebib and Johnston, 2000). GABA is a flexible compound, due to its rotation about the C2-C3 and C3-C4 bonds. It can exist in a range of low energy conformations (Johnston et al, 1978). Analogues of GABA in which two of these conformations have been restricted by the introduction of unsaturation in the form of a double bond at the C2-C3 position have been prepared. Two compounds that represent these restricted conformations are CACA and trans-4-aminocrotonic acid (TACA) (Johnston et al, 1975). CACA and TACA have fewer degrees of rotational freedom than GABA, and can only rotate about the C3-C4 bond (Johnston et al, 1978). CACA is a partially folded analogue of GABA. It has moderate activity at $GABA_C$ receptors expressed in *Xenopus* oocytes, and although its agonist activity is weak, it is to date the most selective agonist at these receptors, having minimal activity on $GABA_A$ and $GABA_B$ receptors (Johnston, 1996b). TACA is an extended analogue of GABA. It has potent agonist activity at $GABA_C$ receptors expressed in *Xenopus* oocytes; however, it is not selective, as it is also a potent $GABA_A$ receptor agonist (Johnston, 1996b).

Woodward et al (1993) tested many GABA analogues on poly $(A)^+$ RNA from mammalian retina expressed in *Xenopus* oocytes to determine a pharmaceutical profile for $GABA_C$ receptors. From this study, it was found that phosphinic and methylphosphinic acid analogues of GABA, which are known to be potent $GABA_B$ receptor agonists, were potent antagonists at $GABA_C$ receptors. Several straight chain phosphinic, methylphosphinic and phosphonic acid analogues of GABA were shown to be potent antagonists at $GABA_C$ receptors, including (3-aminopropyl)methylphosphinc acid (CGP35024, $K_B$=0.8 μM), 3-aminoporpylphosphinic acid (CGP27492, $K_B$=0.8 μM) and 3-aminopropylphosphonic acid (3-APA, $K_B$=1.8 μM) (Woodward et al, 1993). These agents are not selective for $GABA_C$ receptors, as CGP35024 and CGP27492 are also very potent $GABA_B$ receptor agonists, while 3-APA is a $GABA_B$ receptor agonist.

To date, the most potent and selective $GABA_C$ receptor antagonist known is 1,2,5,6-tetrahydropyridine-4-yl)methylphosphinic acid (TPMPA, $K_B$=2.1 μM) (Murata et al, 1996; Ragozzinno et al, 1996). TPMPA produces 50% inhibition of $GABA_C$ receptor activation at 2.1 μM.

Chebib et al, 1997 demonstrated that TPMPA, the phosphinic and methyl phosphinic acid analogues of CACA and the closely related analogue TACA, and 3-aminopropyl-n-butyl-phosphinic acid (CGP36742), an orally active $GABA_B$ receptor antagonist, are $GABA_C$ receptor antagonists.

It has been shown that $GABA_C$ receptor antagonists have therapeutic application.

Froestl et al., 1995 investigated a series of $GABA_B$ receptor antagonists in various memory and learning tests in rats and mice. Only one compound in this series, 3-aminopropyl-n-butyl-phosphinic acid (CGP36742), reversed age related deficits of old rats. The cognition-enhancing effects of this compound were confirmed in learning experiments in monkeys (Froestl et al., 1995).

The cognition-enhancing effects of CGP36742 is not satisfactorily explained by its $GABA_B$ antagonist properties, since much more potent $GABA_B$ antagonists have been described that do not have these effects. Some of the present inventors have previously shown that CGP36742 has similar potency as a $GABA_C$ antagonist to its potency as a $GABA_B$ antagonist (50% inhibition of receptor activation being found at 38 μM and 62 μM against $GABA_B$ and $GABA_C$ receptors respectively) (Chebib et al, 1997). None of the other potent $GABA_B$ antagonists used in Froestl et al., 1995 showed activity against $GABA_C$ receptors. These findings indicate a role for $GABA_C$ receptor antagonism in the cognition-enhancing properties of CGP36742.

WO 98/58939 describes a method of enhancing the cognitive activity of an animal in need of such treatment, comprising the step of administering an effective amount of a compound which has $GABA_C$ receptor antagonist activity to said animal. That document also describes a method of stimulating memory capacity, comprising the step of administering an effective amount of a compound which has $GABA_C$ receptor antagonist activity to an animal in need of such treatment. The document also describes novel compounds having $GABA_C$ receptor antagonist activity of the general formula I and general formula II as defined in that document.

Australian provisional patent application nos. P07501 and PP2985 describe various generic classes of compounds which are said to have $GABA_C$ receptor antagonist activity.

Most of the $GABA_C$ receptor antagonists described in the prior art, such as CGP36742, are non-selective, that is, they also have significant activity at the $GABA_A$ or $GABA_B$ receptors. The use of such compounds as $GABA_C$ receptor antagonists may have undesirable side-effects via their action at the $GABA_A$ and/or $GABA_B$ receptors.

It would be desirable to identify selective antagonists of the GABA$_C$ receptors. Such agents are needed to determine the physiological role of GABA$_C$ receptors and to provide therapeutic agents with a lower risk of unwanted side-effects due to actions at the GABA$_A$ and/or GABA$_B$ receptors.

SUMMARY OF THE INVENTION

The inventors have found a class of compounds which are surprisingly selective GABA$_C$ receptor antagonists. The compounds of the invention also have a lipid solubility which results in an increased ability of the compound to cross the blood brain barrier compared to prior art selective GABA$_C$ receptor antagonists, such as TPMPA.

In one aspect, the present invention provides the compound 3-(aminocyclopentanyl)butylphosphinic acid of the formula I:

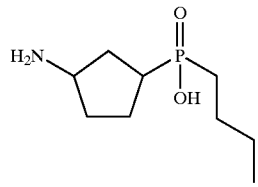

and salts thereof.

In a second aspect, the present invention provides compounds of the formula II:

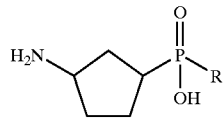

wherein R represents propyl, butyl, pentyl, neo-pentyl or cyclohexyl, and salts thereof.

The compounds of the present invention can exist in various stereoisomers. In particular, cis- and trans-isomers of the compounds can be prepared. The present invention encompasses all stereoisomers of the compounds including racemic mixtures of the cis- or trans-isomers of the compounds, as well as the individual stereoisomers.

For example, the following isomers of 3-(aminocyclopentanyl)butylphosphinic acid can be prepared:

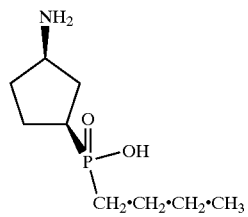 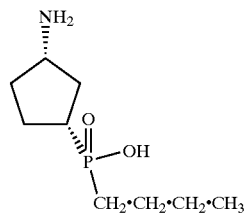

-continued

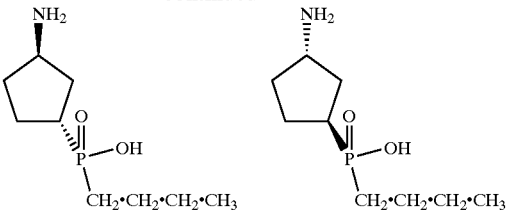

Each of these isomers is encompassed by the present invention.

The compounds of the present invention are GABA analogues that are conformationally restricted by incorporating the backbone of GABA into a cyclopentane ring. This conformational restriction results in a primary amino group in the 3-position of the cyclopentane ring. This conformational restriction makes it difficult for the compounds to act at either GABA$_A$ or GABA$_B$ receptors, making these compounds surprisingly selective GABA$_C$ antagonists.

The compounds of the present invention have a propyl, butyl, pentyl, neo-pentyl or cyclohexyl, preferably a butyl, substituted phosphinic acid group in the 1-position of the cyclopentane ring, corresponding to the carboxylic acid functionality of GABA. This substituent enhances lipid solubility of the compounds of the present invention and thus increases the ability of the compounds to cross the blood brain barrier.

In a third aspect, the present invention provides a method of selectively antagonising GABA$_C$ receptors compared with GABA$_B$ or GABA$_A$ receptors, comprising the step of exposing the receptors to an effective amount of a compound of formula I or formula II as defined above or a pharmaceutically acceptable salt thereof.

In a fourth aspect, the present invention provides a method of enhancing the cognitive activity of an animal, comprising the step of administering to the animal an effective amount of a compound of formula I or formula II as defined above or a pharmaceutically acceptable salt thereof.

In a fifth aspect, the present invention provides a method of stimulating memory capacity in an animal, comprising the step of administering to the animal an effective amount of a compound of formula I or formula II as defined above or a pharmaceutically acceptable salt thereof.

The methods of the invention are suitable for the treatment of a variety of cognitive deficit conditions, dementias and memory impairment conditions, including but not limited to those associated with Alzheimer's disease, AIDS and schizophrenia.

While the invention is not restricted to the treatment of any particular animal species, in general, the animal will be a human.

In another aspect, the present invention provides the use of a compound of formula I or formula II as defined above or a pharmaceutically acceptable salt thereof for the manufacture of a medicament for selectively antagonising GABA$_C$ receptors compared with GABA$_B$ or GABA$_A$ receptors.

In another aspect, the present invention provides the use of a compound of formula I or formula II as defined above or a pharmaceutically acceptable salt thereof for the manufacture of a medicament for enhancing the cognitive activity of an animal.

In another aspect, the present invention provides the use of a compound of formula I or formula II as defined above or a pharmaceutically acceptable salt thereof for the manufacture of a medicament for stimulating memory capacity in an animal.

In another aspect, the present invention provides a pharmaceutical composition comprising a compound of formula I or formula II as defined above or a pharmaceutically acceptable salt thereof, and a pharmaceutically acceptable carrier.

As will be apparent to a person skilled in the art, various salts of compounds of formula I or formula II as defined above can be prepared. Such salts include, for example, metal salts, ammonium salts, salts with an organic base, salts with an inorganic acid, and salts with an organic acid. Examples of metal salts include alkali metal salts, such as a sodium salt or a potassium salt. Examples of salts with an inorganic acid include salts with acids such as hydrochloric acid or hydrobromic acid. Examples of salts with organic acids include salts with acetic acid, trifluoroacetic acid, citric acid or formic acid.

The compounds of formula I or formula II as defined above or pharmaceutically acceptable salts thereof, may be administered to an animal at any suitable dose and by any suitable route. The compounds may, for example, be administered orally or parenterally in dosage unit formulations containing conventional non-toxic pharmaceutically acceptable carriers. The term "parenteral" as used herein includes subcutaneous injections, aerosol, intravenous, intramuscular, intrathecal, intracranial injection or infusion techniques. Oral administration is preferred because of its greater convenience and acceptability.

Suitable pharmaceutical compositions for administration by any desired route may be prepared by standard methods using pharmaceutically acceptable carriers known in the art, for example by reference to well known texts such as Remington: The Science and Practice of Pharmacy, 2000 (20$^{th}$ Edition), AR Gennaro (Ed), Lippincott Williams & Wilkins, Philadelphia, Pa. 19106-3621, USA or Australian Prescription Products Guide, 2000 (29$^{th}$ Edition), J Thomas (Ed), Australian Pharmaceutical Publishing Company Limited, Victoria, Australia.

The pharmaceutical compositions of the present invention may be formulated for oral administration as tablets, aqueous or oily suspensions, lozenges, troches, powders, granules, emulsions, capsules, syrups or elixirs. Compositions formulated for oral administration, may contain one or more agents selected from the group of sweetening agents, flavouring agents, colouring agents and preserving agents in order to produce pharmaceutically elegant and palatable preparations.

When the pharmaceutical composition of the present invention is in the form of a tablet suitable for oral administration, the tablet typically contains the compound of formula I or II as defined above or pharmaceutically acceptable salt thereof in admixture with one or more pharmaceutically acceptable carriers. These pharmaceutically acceptable carriers may include, for example, (1) inert diluents, such as calcium carbonate, lactose, calcium phosphate or sodium phosphate; (2) granulating and disintegrating agents, such as corn starch or alginic acid; (3) binding agents, such as starch, gelatine or acacia; and (4) lubricating agents, such as magnesium stearate, stearic acid or talc. The tablets may be uncoated or coated by known techniques to delay disintegration and absorption in the gastrointestinal tract and thereby provide a sustained action over a longer period. For example, a time delay material such as glyceryl monostearate or glycol distearate may be employed.

Pharmaceutical compositions for parenteral administration are typically in the form of sterile aqueous or non-aqueous solutions, suspensions, or emulsions. Suitable pharmaceutically acceptable carriers for such compositions include non-aqueous carriers such as propylene glycol, polyethylene glycol, vegetable oils such as olive oil, and injectable organic esters such as ethyl oleate, and aqueous carriers such as water and alcoholic/aqueous solutions, including saline and buffered media. The pharmaceutical composition may also include preservatives and other additives such as, for example, anti-microbials, anti-oxidants, chelating agents, and the like.

The effective amount of the compound will depend on the nature of the condition to be treated, and the age, weight and underlying state of health of the individual to be treated, and the dosage administered will be at the discretion of the attending physician or veterinarian. The effective amount may readily be determined by those skilled in the art by trial and error experimentation, using methods which are well known in the art.

BRIEF DESCRIPTION OF THE DRAWINGS

FIG. 3 shows the structure and $^1$H-NMR spectrum of (±)-cis-(3-aminocyclopentanyl)butylphosphinic acid ((±)-cis-ACPBPA). The spectrum was recorded in deuterated water (D$_2$O) at 300 MHz using a Varian Gemini 300 spectrometer. Chemical shifts ($\delta_H$) are quoted in ppm and referenced externally to TMS at 0 ppm. An asterisk (*) denotes a chiral centre in the compound.

Figure 10:
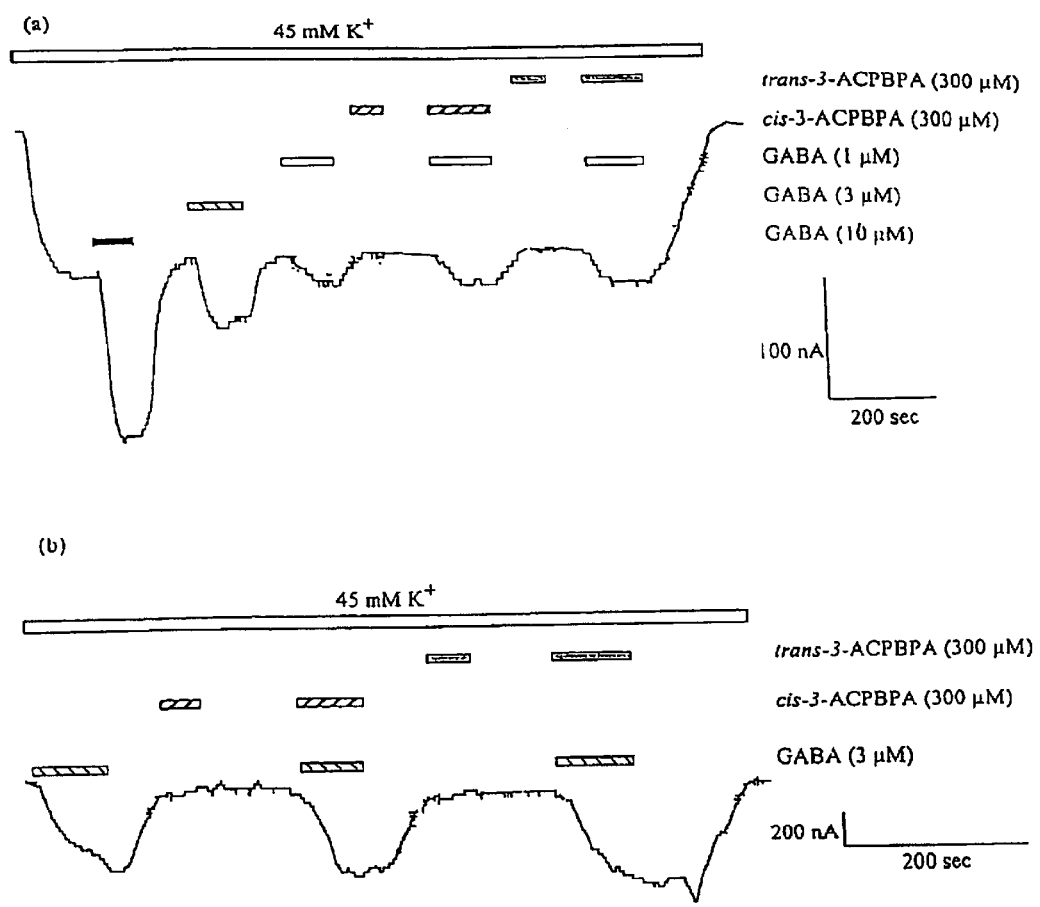

FIG. 10 shows the current responses in the presence of K$^+$(45 mm) of
(a) GABA$_B$ (1b,2) receptors expressed in Xenopus oocytes clamped at −60 mV, in the presence of GABA (10 μM) (duration indicated by black filled bar), a solution of GABA (3 μM) (duration indicated by lightly hatched bar) and GABA (1 μM) (duration indicated by open bar) alone, cis-3-ACPBPA (300 μM) (duration indicated by heavily hatched bar) alone, cis-3-ACPBPA (300 μM) co-applied with GABA (1 μM), trans-3-ACPBPA (300 μM) (duration indicated by grey shaded bar) alone and trans-3-ACPBPA (300 μM) co-applied with GABA (1 μM); and
(b) GABA$_B$ (1a,2) receptors expressed in Xenopus oocytes clamped at 60 mV, in the presence of GABA (3 μM) (duration indicated by lightly hatched bar) alone, cis-3-ACPBPA (300 μM) (duration indicated by heavily hatched bar) alone, cis-3-ACPBPA (300 μM) co-applied with GABA (3 μM), trans-3-ACPBPA (300 μM) (duration indicated by grey shaded bar) alone and trans-3-ACPBPA (300 μM) co-applied with GABA (3 μM).

Figure 11:
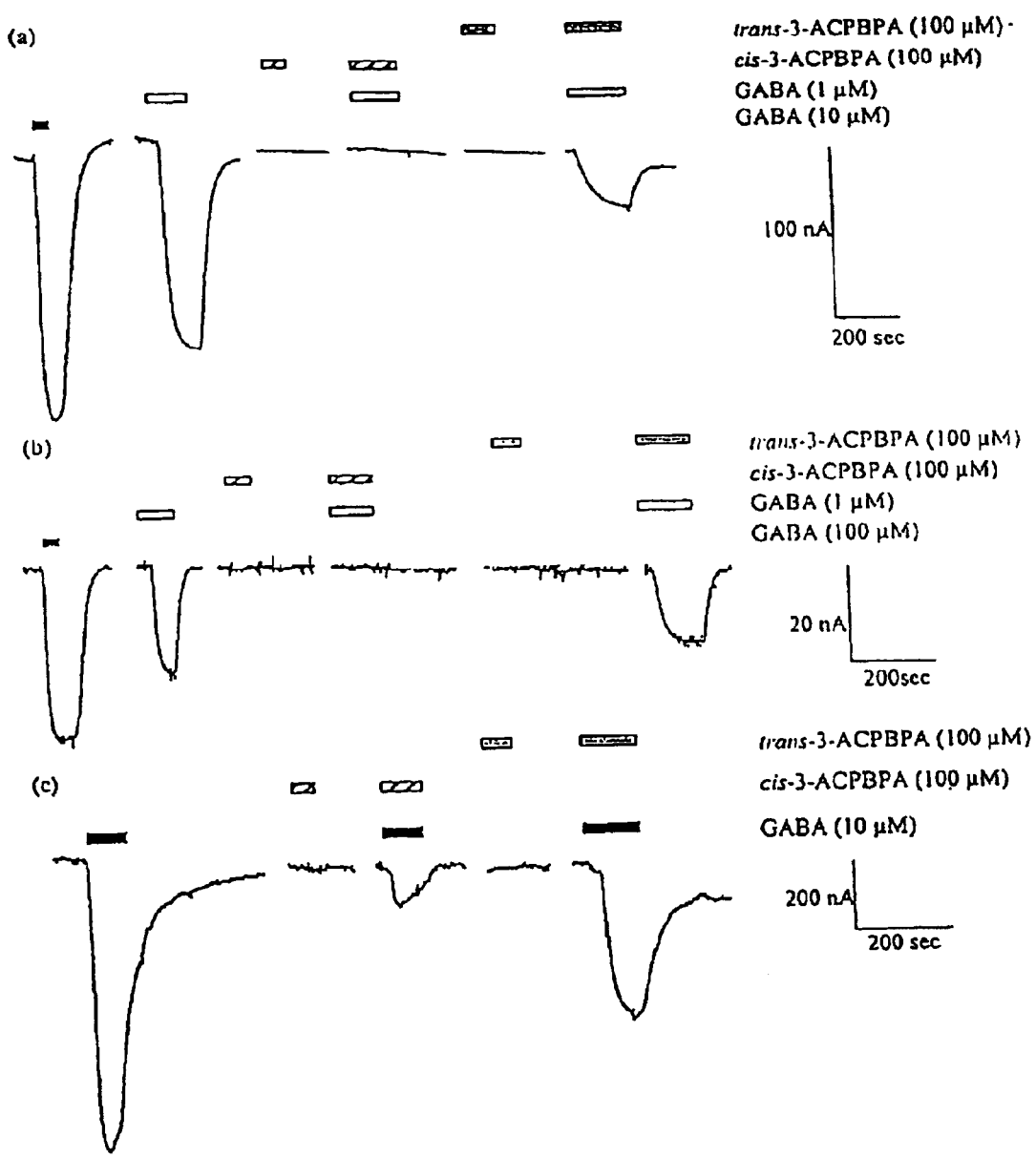

FIG. 11 shows the current responses in the presence of ND96 of
(a) GABA$_C$ (ρ1) receptors expressed in Xenopus oocytes clamped at −60 mV, in the presence of GABA (10 μM (duration indicated by black filled bar) alone, GABA (1 μM) alone (duration indicated by open bar), cis-3-ACPBPA (100 μM) (duration indicated by heavily hatched bar) alone, cis-3-ACPBPA (100 μM) co-applied with GABA (1 μM), trans-3-ACPBPA (100 μM) (duration indicated by grey shaded bar) alone, and trans-3-ACPBPA (100 μM) co-applied with GABA (1 μM).
(b) GABA$_C$ (ρ2) receptors expressed in Xenopus oocytes clamped at −60 mV, in the presence of GABA (100 μM) (duration indicated by black filled bar) alone, GABA (1 μM) alone (open bar), cis-3-ACPBPA (100/μM) (duration indicated by heavily hatched bar) alone, cis-3-ACPBPA (100 μM) co-applied with GABA (1 μM), trans-3-ACPBPA (100 μM) (duration indicated by grey shaded bar) alone, and trans-3-ACPBPA (100 μM) co-applied with GABA (1 μM.
(c) GABA$_C$) (ρ3) receptors expressed in Xenopus oocytes clamped at −60 mV, in the presence of GABA (10 μM) (duration indicated by black filled bar) alone, cis-3-ACPBPA (100 μM) (duration indicated by heavily hatched bar) alone, cis-3-ACPBPA (100 μM) co-applied with GABA (10 μM), trans-3-ACPBPA (100 μM) (duration indicated by grey shaded bar) alone, and trans-3-ACPBPA (100 μM) co-applied with GABA (10 μM).

Figure 12:
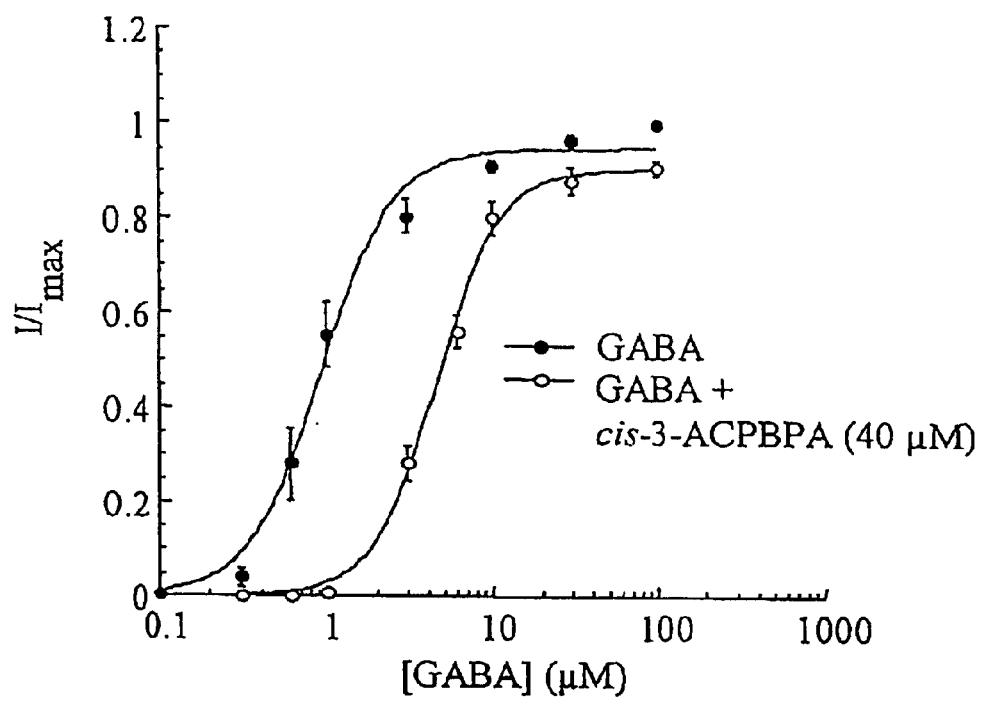
Figure 12:
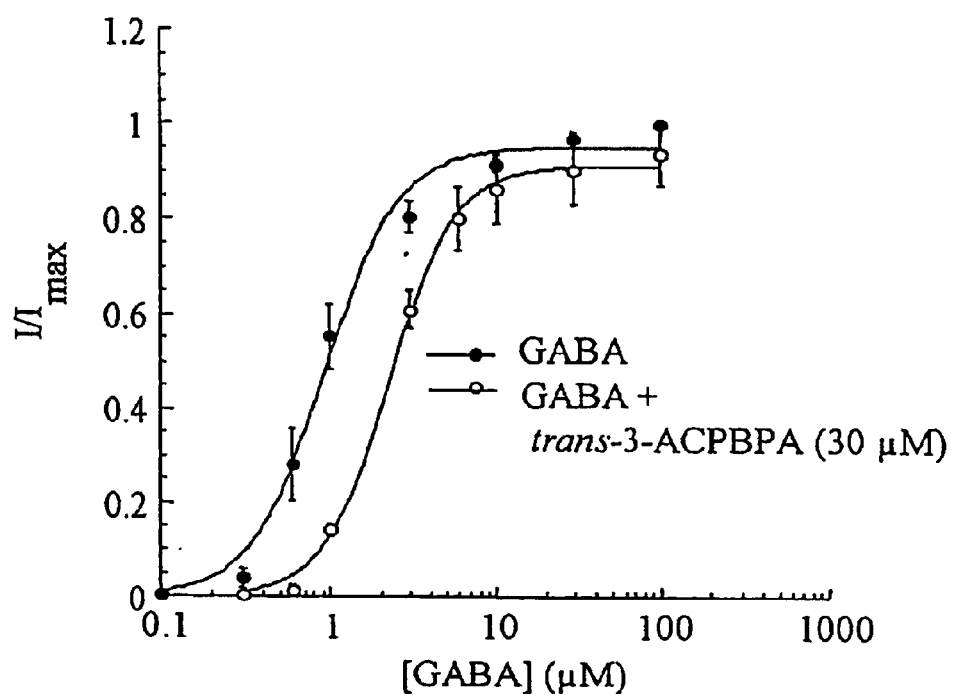

FIG. 12 shows dose response curves at the GABA$_C$ ρ1 receptor expressed in Xenopus oocytes. FIG. 12(a) shows the dose response curve for GABA alone and in the presence of 40 μM (÷)-cis-ACPBPA. FIG. 12(b) shows the dose response curve for GABA alone and in the presence of 30 μM (±)-trans-ACPBPA. Data are means±s.e mean (n=3.4 oocytes).

DETAILED DESCRIPTION OF THE INVENTION

The invention is described below in detail by way of reference only to the following non-limiting Examples, and to the Figures.

EXAMPLE 1

Synthesis of (±)-cis- and (±)-trans-3-(aminocyclopentanyl)butylphosphinic acid.

Described below is the synthesis of (±)-cis- and (±)-trans-3-(aminocyclopentanyl)butylphosphinic acid. Other compounds of the present invention can be prepared by a similar process.

Note that the racemic compounds were synthesised. Unless otherwise noted, the duplication of peaks in the NMR spectra arises from the presence of diastereoisomers associated with the chirality of the phosphorus atom in the phosphinic ester.

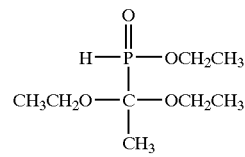

1

Ethyl (1,1-diethoxyethyl)phosphinate (1)

The product, ethyl (1,1-diethoxyethyl)phosphinate (1) was prepared as described by Froestl et al (Froestl et al, 1995), and the chemical synthesis was commenced from this product.

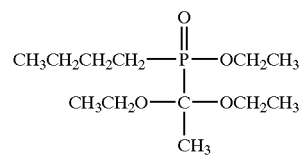

2

Synthesis of ethyl (1,1-diethoxyethyl)butylphosphinate (2)

A solution of ethyl (1,1-diethoxyethyl)phosphinate (1) (30.2 g, 0.113 mol) in anhydrous THF (100 cm$^3$) was added dropwise to a solution of sodium anhydride (6.2 g, 0.258 mol) in anhydrous THF (200 cm$^3$). The resulting reaction mixture was cooled to 0° C. and allowed to stir for 1 hour. Then a solution of 1-iodobutane (42 cm$^3$) in anhydrous THF (20 cm$^3$) was added to the reaction mixture dropwise and left to stir overnight. Following this, the solvent was then removed in vacuo. The residue was partitioned between DCM (50 cm$^3$) and water (30 cm$^3$) and the aqueous layer was further extracted with DCM (3×20 cm$^3$). The combined organic layers were washed with water (2×30 cm$^3$) and brine (40 cm$^3$) and dried over anhydrous sodium sulfate, filtered and the solvent removed in vacuo. Purification by short column vacuum chromatography was not required as confirmed by $^1$H-NMR, resulting with the desired title compound (2) as a yellow oil (29.28 g, 77%): $^1$H-NMR (300 MHz, CDCl$_3$) δ$_H$ 0.90 (3H, 2×d, J=7.2 and 7.5 Hz, PCH$_2$CH$_2$CH$_2$CH$_3$), 1.17 (6H, 2×d, J=7.2 and 7.2 Hz, (CH$_3$CH$_2$O)$_2$CCH$_3$), 1.20 (6H, 2×d, J=6.9 and 6.9 Hz, (CH$_3$CH$_2$O)$_2$CCH$_3$), 1.29 (3H, t, J=7.2 and 7.2 Hz, POCH$_2$CH$_3$), 1.38 (2H, m, PCH$_2$CH$_2$CH$_2$CH$_3$), 1.47 (3H, d, J=11.1 Hz, (CH$_3$CH$_2$O)$_2$CCH$_3$), 1.66 (4H, m, PCH$_2$CH$_2$CH$_2$CH$_3$),3.67 (4H, m, (CH$_3$CH$_2$O)$_2$CCH$_3$), 4.19 (2H, m, POCH$_2$CH$_3$).

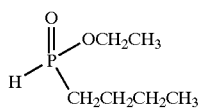

3

Synthesis of ethyl butylphosphinate (3)

A solution of ethyl (1,1-diethoxyethyl)butylphosphinate (2) (29.3 g, 0.110 mol) in DCM (150 cm$^3$) was dried over anhydrous sodium sulfate, filtered and the solvent removed in vacuo. To the resulting product was added DCM (150 cm$^3$) and ethanol (15 cm$^3$). The reaction mixture was cooled to 0° C. and trimethylsilyl chloride (21 cm$^3$) was added dropwise with constant stirring. The resulting reaction mixture was then stored below 0–4° C. and a second addition of trimethylsilyl chloride (23 cm$^3$) was made. Purification by short column vacuum chromatography was not required as confirmed by $^1$H-NMR, resulting with the desired title compound (3) as a pale yellow oil (21.02 g, 100%): $^1$H-NMR (300 MHz, CDCl$_3$) $\delta_H$ 0.89 (3H, 2×d, PCH$_2$CH$_2$CH$_2$CH$_3$), 1.12–1.81 (9H, m, POCH$_2$CH$_3$, PCH$_2$CH$_2$CH$_2$CH$_3$, PCH$_2$CH$_2$CH$_2$CH$_3$, PCH$_2$CH$_2$CH$_2$CH$_3$),4.12 (2H, m, POCH$_2$CH$_3$) 6.19 and 7.93 (1H, d, J=522 Hz, P—H); $^{13}$C-NMR (75 MHz, CDCl$_3$) $\delta_C$ 8.84 (s, PCH$_2$CH$_2$CH$_2$CH$_3$), 11.52 and 11.60 (d, $^3$J$_{POCC}$=6 Hz, POCH$_2$CH$_3$), 18.05 and 18.09 (d, $^2$J$_{PC}$=3.15 Hz, PCH$_2$CH$_2$CH$_2$CH$_3$), 18.74 and 18.96 (d, $^3$J$_{PC}$=15.98 Hz, PCH$_2$CH$_2$CH$_2$CH$_3$), 23.06 and 24.30 (d, J$_{PC}$=93.3 Hz, PCH$_2$CH$_2$CH$_2$CH$_3$), 57.67 and 57.76 (d, $^2$J$_{POC}$=6.83 Hz, POCH$_2$CH$_3$); $^{31}$P-NMR (121 MHz, CDCl$_3$) $\delta_H$ 40.37; MS (CI, CH$_4$) m/z 151.0 (100%) (MH$^+$), 300.9 (38),123.1 (35),195.1 (12).

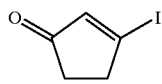

5

Synthesis of 3-iodo-2-cyclopenten-1-one (5)

A solution of triphenylphosphine (32.1 g, 0.123 mol) and iodine (31.2 g, 0.123 mol) in acetonitrile (500 cm$^3$) was stirred at room temperature for 2 hours. To the resulting orange suspension, triethylamine (12.4 g, 0.118 mol) and 1,3-cyclopentadione (10 g, 0.102 mol) were added. The reaction mixture was then heated at reflux for 3 hours, cooled to room temperature and the solvent removed in vacuo. The residual material was purified by short column vacuum chromatography on silica gel with (diethyl ether/petroleum ether=1:1), to yield the desired title compound (5) as a pale yellow solid (17.69 g, 83%): $^1$H-NMR (300 MHz, CDCl$_3$) $\delta_H$ 2.49 (2H, m, C(5)—H and C(5)—H'), 3.05 (2H, m, C(4)—H and C(4)—H'), 6.67 (1H, s, C(2)—H).

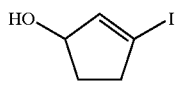

6

Synthesis of (±)-3-iodo-2-cyclopenten-1-ol (6)

A solution of 3-iodo-2-cyclopenten-1-one (5) (16.5 g, 79.3 mmol) in ethanol (250 cm$^3$) was cooled to 0° C. and sodium borohydride (1.5 g, 39.6 mmol) was added in small portions over 1 hour. When the addition was complete the reaction was monitored via TLC as the temperature returned to room temperature. When the reaction was complete, indicated via TLC, acetone (25 cm$^3$) was added and the solvent removed in vacuo. The residue was partitioned between DCM (200 cm$^3$) and water (35 cm$^3$) and the aqueous layer was further extracted with DCM (3×50 cm$^3$). The combined organic layers were washed with brine (50 cm$^3$), dried over anhydrous magnesium sulfate, filtered and the solvent removed in vacuo. Purification by short column vacuum chromatography was not required as confirmed by $^1$H-NMR, resulting with the desired title compound (6) as a pale yellow oil (12.70 g, 77%): $^1$H-NMR (300 MHz, CDCl$_3$) $\delta_H$ 1.76 and 2.35 (2H, m, C(4)—H and C(4)—H'), 2.58 and 2.83 (2H, m, C(5)—H and C(5)—H'), 3.70 (1H, r, C(1)—H), 4.71 (1H, br. s, C(1)—OH), 6.23 (1H, s, C(2)—H).

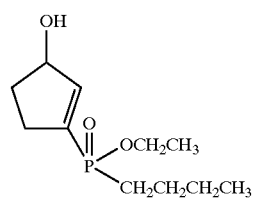

7

The synthesis of (±)-ethyl (3-hydroxycyclopentenyl)butylphosphinate (7), as the common intermediate, was carried out in duplication so that one reaction scheme would eventuate with the synthesis of (±)-cis-3-ACPBPA and the other scheme with (±)-trans-3-ACPBPA.

Synthesis of (±)-ethyl (3-hydroxycyclopentenyl)butylphosphinate (7)

A solution of DABCO (11.8 g, 0.105 mol) in anhydrous toluene (300 cm$^3$) was heated at reflux for 1 hour with continual stirring. The solution was allowed to cool to room temperature, to which (±)-3-iodo-2-cyclopenten-1-ol (6) (6.35 g, 30.4 mmol) was added. Following this, trimethylsilyl chloride (4 mL) was added slowly, after which the reaction mixture was allowed to stir for 15 minutes. On the side, a solution of ethyl butylphosphinate (3) (21.0 g, 0.140 mol) in DCM (150 cm$^3$) was dried over anhydrous sodium sulfate, filtered and the solvent removed in vacuo. Following this, ethyl butylphosphinate (6.83 g, 45.5 mmol) and tetrakis(triphenylphosphine)palladium(0) (876 mg, 2.5 mol %) were then added to the reaction mixture. The reaction mixture was heated at 70° C. for 24 hours after which a second portion of tetrakis(triphenylphosphine)-palladium(0) (876 mg, 2.5 mol %) was added and heating continued for a further 24 hours. The reaction mixture was filtered while still hot and aqueous ethanol (100 cm$^3$), followed by acetic acid (10 cm$^3$) were added to the filtrate, which were then concentrated in vacuo. The product was isolated by short column vacuum chromatography on silica gel (10% ethanol/ethyl acetate) to yield the title compound (7) as a pale yellow oil (4.74 g, 67%; 4.45 g, 63%): $^1$H-NMR (300 MHz, CDCl$_3$) $\delta_H$ 0.87 (3H, 2×t, J=7.2 and 7.2 Hz & 7.2 and 7.2 Hz, PCH$_2$CH$_2$CH$_2$CH$_3$), 1.17–1.89 (10H, m, C(5)—H', POCH$_2$CH$_3$, PCH$_2$CH$_2$CH$_2$CH$_3$, PCH$_2$CH$_2$CH$_2$CH$_3$, PCH$_2$CH$_2$CH$_2$CH$_3$), 2.37 (2H, m, C(5)—H and C(4)—H'), 2.62 (1H, m, C(4)—H), 3.45 (1H, br. s, C(3)—OH), 4.02 (2H, m, POCH$_2$CH$_3$),4.95 (1H, m, C(3)—H), 6.62 (1H, d, J=9.7 Hz, C(2)—H); $^{13}$C-NMR (75 MHz, CDCl$_3$) $\delta_C$ 13.45 (s, PCH$_2$CH$_2$CH$_2$CH$_3$),16.39 and 16.47 (d, $^3$J$_{POCC}$=6.23 Hz, POCH$_2$CH$_3$), 23.32 and 23.36 (d, $^2$J$_{PC}$=3.38 Hz, PCH$_2$CH$_2$CH$_2$CH$_3$), 23.64 and 23.86 (d, $^3$J$_{PC}$=15.98 Hz, PCH$_2$CH$_2$CH$_2$CH$_3$), 27.10 and 28.30 (d, J$_{PC}$=90.23 Hz, PCH$_2$CH$_2$CH$_2$CH$_3$), 31.65 and 31.80 (d, $^3$J$_{PC}$=11.70 Hz, C(4)), 33.89 and 33.95 (d, $^2$J$_{PC}$=4.58 Hz, C(5)), 60.55 (s, POCH$_2$CH$_3$), 76.61 and 77.03 (d, $^3J_{PC}$=31.58 Hz, C(3)), 136.94 and 138.51 (d, J$_{PC}$=117.3 Hz, C(1)), 148.81 (s, C(2)); $^{31}$P-NMR (121 MHz, CDCl$_3$) δ$_P$ 43.93 and 44.18; MS (CI, CH$_4$) m/z 233.1 (100%) (MH$^+$), 215.2 (47), 464.9 (39), 261.2 (18).

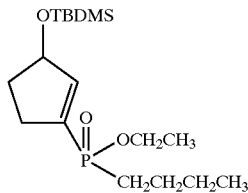

8

Synthesis of (±)-ethyl [3-(t-butyldimethylsilyloxy) cyclopentenyl]butylphosphinate (8)

A solution of (±)-ethyl (3-hydroxycyclopentenyl) butylphosphinate (7) (3.66 g, 15.8 mmol) in anhydrous DMF (100 cm$^3$) was treated with t-butyldimethylsilyl chloride (2.62 g, 17.4 mmol), triethylamine (4.55 cm$^3$) and DMAP (425 mg). The reaction mixture was stirred at room temperature for 16 h, after which time the solvent was removed in vacuo. The residue was partitioned between DCM (50 cm$^3$) and water (30 cm$^3$) and the aqueous layer was further extracted with DCM (3×20 cm$^3$). The combined organic layers were washed with water (2×30 cm$^3$) and brine (40 cm$^3$), dried over anhydrous sodium sulfate, filtered and the solvent removed under reduced pressure. The crude product was purified by short column vacuum chromatography on silica gel (15% ethanol/ethyl acetate) to yield the desired title compound (8) as a colourless oil (3.35 g, 61%): $^1$H-NMR (300 MHz, CDCl$_3$) δ$_H$ 0.09 (6H, s, Si(CH$_3$)$_2$), 0.89 (9H, s, SiC(CH$_3$)$_3$), 0.91 and 0.93 (3H, 2×d, J=7.2 Hz, PCH$_2$CH$_2$CH$_2$CH$_3$), 1.22–1.83 (9H, m, POCH$_2$CH$_3$, PCH$_2$CH$_2$CH$_2$CH$_3$, PCH$_2$CH$_2$CH$_2$CH$_3$, PCH$_2$CH$_2$CH$_2$CH$_3$), 2.26–2.72 (4H, m, C(4)—H, C(4)—H', C(5)—H and C(5)—H'), 3.84–4.19 (2H, m, POCH$_2$CH$_3$), 4.97 (1H, m, C(3)—H), 6.50 and 6.54 (1H, 2×d, J=9.6 and 9.6 Hz, C(2)—H); $^{13}$C-NMR (75 MHz, CDCl$_3$) δ$_C$ -4.81 and -4.74 (d, $^6J_{PC}$=5.7 Hz, Si(CH$_3$)$_2$), 13.48 (s, PCH$_2$CH$_2$CH$_2$CH$_3$), 16.43 and 16.51 (d, $^6J_{PC}$=6.23 Hz, SiC(CH$_3$)$_3$), 18.08 (s, POCH$_2$CH$_3$), 23.43 (t, $^2J_{PC}$=3.15 and 3.15 Hz, PCH$_2$CH$_2$CH$_2$CH$_3$), 23.69 and 23.90 (d, $^3J_{PC}$=15.90 Hz, PCH$_2$CH$_2$CH$_2$CH$_3$), 25.75 (s, SiC(CH$_3$)$_3$), 27.22 and 28.54 (2×d, J$_{PC}$=99.6 and 99.0 Hz, PCH$_2$CH$_2$CH$_2$CH$_3$), 31.55 and 31.70 (2×d, $^3J_{PC}$=11.63 and 11.63 Hz, C(4)), 34.54 (t, $^2J_{PC}$=8.25 and 8.55 Hz, C(5)), 60.15 (2×d, 2J$_{POC}$= 6.30 and 6.83 Hz, POCH$_2$CH$_3$), 77.97 and 78.22 (d, $^3J_{PC}$= 18.45 Hz, C(3)), 136.64 and 138.24 (2×d, J$_{PC}$=119.78 and 120.08 Hz, C(1)), 148.51 (d, $^2J_{PC}$=9.38 Hz, C(2)); 31P-NMR (121 MHz, CDCl$_3$) δ$_P$ 42.77 and 43.15; MS (CI, CH$_4$) m/z 347.2 (16%) (MH$^+$), 215.1 (100), 375.3 (44), 289.2 (39).

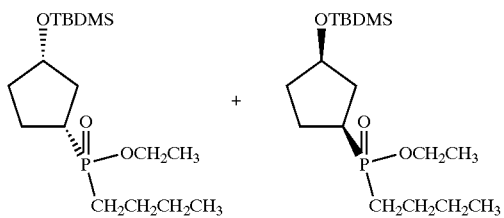

9

Synthesis of (±)-cis-ethyl [3(t-butyldimethylsilyloxy) cyclopentanyl]butylphosphinate (9)

A solution of (±)-ethyl [3-(t-butyldimethylsilyloxy) cyclopentenyl]butylphosphinate (8) (3.20 g, 9.23 mmol) in ethanol (30 cm$^3$) was hydrogenated over palladium on carbon (50 mg) at 40 psi for 3 hours. The catalyst was removed by filtration through celite, which was washed with methanol (3×30 cm$^3$). The solvent was removed in vacuo to yield the desired title compound (9) in quantitative yield (>90% cis isomer (9) by NMR spectroscopy) as a colourless oil, which was used in the next step without further purification (2.55g, 79%) (data for cis isomer only is reported): $^1$H-NMR (300 MHz, CDCl$_3$) δ$_H$ 0.05 (6H, s, Si(CH$_3$)$_2$), 0.89 (9H, s, SiC(CH$_3$)$_3$), 0.90 and 0.92 (3H, 2×d, J=7.2 and 9.3 Hz, PCH$_2$CH$_2$CH$_2$CH$_3$), 1.23–2.21 (16H, m, C(1)—H, C(2)—H, C(2)—H', C(4)—H, C(4)—H', C(5)—H and C(5)—H', POCH$_2$CH$_3$, PCH$_2$CH$_2$CH$_2$CH$_3$, PCH$_2$CH$_2$CH$_2$CH$_3$, PCH$_2$CH$_2$CH$_2$CH$_3$), 3.99–4.35 (3H, m, POCH$_2$CH$_3$, C(3)—H); $^{13}$C-NMR (75 MHz, CDCl$_3$) δ$_C$ -4.89 and -4.87 (d, $^6J_{PC}$=1.43 Hz, Si(CH$_3$)$_2$), 13.51 (s, PCH$_2$CH$_2$CH$_2$CH$_3$), 16.63 and 16.70 (d, $^6J_{PC}$=5.4 Hz, SiC (CH$_3$)$_3$), 17.98 (s, POCH$_2$CH$_3$), 23.60 and 23.77 (2×d, $^3J_{PC}$=12.75 and 13.13 Hz, PCH$_2$CH$_2$CH$_2$CH$_3$), 23.91 (s, C(5)), 24.10 (s, PCH$_2$CH$_2$CH$_2$CH$_3$), 25.74 (s, SiC(CH$_3$)$_3$), 25.26 and 26.47 (2×d, J$_{PC}$=89.10 and 92.18 Hz, PCH$_2$CH$_2$CH$_2$CH$_3$), 34.88 and 36.51(2×d, J$_{PC}$=4.50 and 94.73 Hz, C(1)), 35.78 and 35.58 (d, $^3J_{PC}$=15.38 Hz, C(4)), 35.86 (s, C(2)), 60.05 (2×d, $^2J_{POC}$=5.93 and 6.30 Hz, POCH$_2$CH$_3$), 73.81 and 73.97 (2×d, $^3J_{PC}$=11.93 and 11.93 Hz, C(3)); $^{31}$P-NMR (121 MHz, CDCl$_3$) δ$_P$ 60.26 and 60.43; MS (CI, CH$_4$) m/z 349.2 (100%) (MH$^+$), 333.3 (40), 291.2 (36), 350.2 (23).

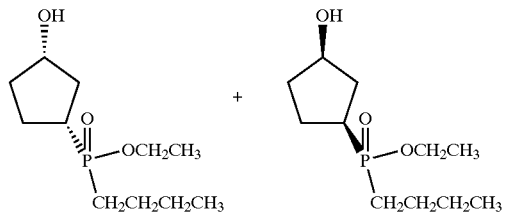

10

Synthesis of (±)-cis-ethyl (3-hydroxycyclopentanyl) butylphosphinate (10)

To a solution of (±)-cis-ethyl [3-(t-butyldimethylsilyloxy) cyclopentanyl]butylphosphinate (9) (2.40 g, 6.89 mmol) in anhydrous THF (30 cm$^3$) was added tetrabutylammonium fluoride (11 cm$^3$ of a 1M solution in anhydrous THF). The reaction mixture was stirred at room temperature for 12 hours, at which time the solvent was removed in vacuo. The crude product was purified by short column vacuum chromatography on silica gel (15% ethanol/ethyl acetate); earlier fractions contained the trans isomer, later fractions contained the desired title cis isomer (10) as a colourless oil (1.39 g, 86%): $^1$H-NMR (300 MHz, CDCl$_3$) δ$_H$ 0.93 (3H, 2×d, J=7.2 and 7.5 Hz, PCH$_2$CH$_2$CH$_2$CH$_3$), 1.20–2.38 (16H, m, C(1)—H, C(2)—H, C(2)—H', C(4)—H, C(4)—H', C(5)—H and C(5)—H', POCH$_2$CH$_3$, PCH$_2$CH$_2$CH$_2$CH$_3$, PCH$_2$CH$_2$CH$_2$CH$_3$, PCH$_2$CH$_2$CH$_2$CH$_3$),3.98–4.40 (4H, m, POCH$_2$CH$_3$, C(3)—OH, C(3)—H); $^{13}$C-NMR (75 MHz, CDCl$_3$) δ$_C$ 13.35 (s, PCH$_2$CH$_2$CH$_2$CH$_3$); 16.50 and 16.57 (d, $^3J_{PC}$=5.4 Hz, POCH$_2$CH$_3$),22.89 and 22.95 (d, $^2J_{PC}$=4.28 Hz, C(5)), 23.42 and 23.68 (d, $^3J_{PC}$=19.35 Hz, PCH$_2$CH$_2$CH$_2$CH$_3$), 23.87 (s, PCH$_2$CH$_2$CH$_2$CH$_3$), 25.45–27.29 (2×d, J$_{PC}$=88.2 and 87.9 Hz, C(1)), 33.99 and 34.08 (d, $^3J_{PC}$=6.53 Hz, C(4)), 35.38 (s, C(2)), 60.57 and 60.66 (2×d, $^2J_{POC}$=6.83 and 6.83 Hz, POCH$_2$CH$_3$), 72.58 and 73.07 (2×d, $^3J_{PC}$=36.15 and 37.28 Hz, C(3)); $^{31}$P-NMR (121 MHz, CDCl$_3$) $\delta_P$ 62.99 and 63.02; MS (CI, CH$_4$) m/z 235.1 (100%) (MH$^+$), 217.1 (50), 263.2 (21), 189.2(16).

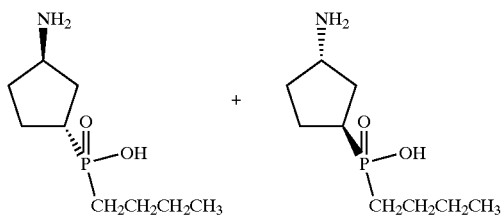

Synthesis of (±)-trans-(3-aminocyclopentanyl) butylphosphinic acid (11)

To a solution of (±)-cis-ethyl (3-hydroxycyclopentanyl) butylphosphinate (10) (1.24 g, 5.29 mmol), DEAD (1.7 cm$^3$) and HN$_3$ (5.6 cm$^3$ of a 1.9 M solution of benzene) in anhydrous THF (50 cm$^3$) under an atmosphere of N$_2$ at 0° C. was added triphenylphosphine (5.52 g, 21.1 mmol) in small portions over a period of 1 hour. The reaction mixture was allowed to warm to room temperature and stirring was continued for 12 hours. The reaction mixture was then heated to 50° C. for 3 hours, then water (2 cm$^3$) was added and heating continued for a further 2 hours. The reaction mixture was cooled to room temperature and the solvent removed in vacuo. The residue was partitioned between aqueous HCl (1 M, 30 cm$^3$) and DCM (30 cm$^3$). The organic layer was separated and further extracted with water (3×30 cm$^3$). The combined aqueous fractions were washed with DCM (2×30 cm$^3$) and concentrated in vacuo. The crude amino ester hydrochloride salt was hydrolysed by refluxing in aqueous HCl (6 M) for 30 hours after which time the reaction mixture was cooled to room temperature and the aqueous HCl removed under reduced pressure. The crude product was purified by ion exchange chromatography (Dowex 50, H$^+$), eluting first with water until the eluate was colourless and the pH 7. On further elution with aqueous pyridine (1 M), ninhydrin positive fractions were collected and the solvent was removed in vacuo. The residual traces of pyridine were removed by repeatedly redissolving the compound in water (20 cm$^3$) and re-evaporating (3 times). Recrystallisation from ethanol/acetone followed by drying gave the desired title compound (11) as a pale yellow solid (535 mg, 49%, m.p. (dec.) 145–148° C.): $^1$H-NMR (300 MHz, D$_2$O) $\delta_H$ 0.78 (3H, t, J=7.2 and 7.2 Hz, PCH$_2$CH$_2$CH$_2$CH$_3$),1.02–2.24 (13H, m, C(1)—H, C(2)—H, C(2)—H', C(4)—H, C(4)—H', C(5)—H and C(5)—H', PCH$_2$CH$_2$CH$_2$CH$_3$, PCH$_2$CH$_2$CH$_2$CH$_3$, PCH$_2$CH$_2$CH$_2$CH$_3$),3.61 (1H, m, C(3)—H); $^{13}$C-NMR (75 MHz, D$_2$O) $\delta_C$ 13.45 (s, PCH$_2$CH$_2$CH$_2$CH$_3$), 24.08 and 24.29 (d, $^3J_{PC}$=15.46 Hz, PCH$_2$CH$_2$CH$_2$CH$_3$), 24.29 and 24.35 (d, $^2J_{PC}$=5.15 Hz, PCH$_2$CH$_2$CH$_2$CH$_3$), 25.31 (s, C(5)), 27.90 and 29.11 (d, J$_{PC}$=91.04 Hz, PCH$_2$CH$_2$CH$_2$CH$_3$), 31.38 (s, C(2)), 31.72 and 31.84 (d, $^3J_{PC}$=9.45 Hz, C(4)), 35.90 and 37.16 (d, J$_{PC}$=95.05 Hz, C(1)), 52.76 and 52.90 (d, $^3J_{PC}$=10.59 Hz, C(3)); $^{31}$P-NMR (121 MHz, D$_2$O) $\delta_P$ 51.41; MS (ESI) m/z 206.4 (28%) (MH$^+$), 166.9 (100), 102.4 (82), 411.3 (58).

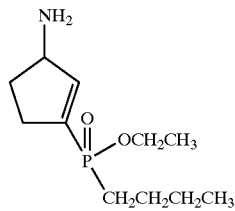

Synthesis of (±)-ethyl (3-aminocyclopentenyl) butylphosphinate (12)

To a solution of (±)-ethyl (3-hydroxycyclopentenyl) butylphosphinate (7) (2.98 g, 12.8 mmol), DEAD (4.2 cm$^3$) and HN$_3$ (13.5 cm$^3$ of a 1.9 M solution in benzene) in anhydrous THF (150 cm$^3$) at 0° C. was added triphenylphosphine (13.43 g, 51.4 mmol) in small portions over a period of 1 hour. The reaction mixture was allowed to warm to room temperature and stirring continued for 12 hours. The reaction mixture was then heated to 50° C. for 3 hours after which time then water (2 cm$^3$) was added and heating continued for a further 2 hours. The reaction mixture was cooled to room temperature and the solvent removed in vacuo. The residue was partitioned between aqueous HCl (1 M, 40 cm$^3$) and DCM (40 cm$^3$). The organic layer was separated and further extracted with water (3×30 cm$^3$). The combined aqueous fractions were washed with DCM (2×30 cm$^3$) and concentrated in vacuo. The crude product was purified by ion exchange chromatography (Dowex 50, H$^+$), eluting first with water until the eluate was colourless and the pH 7. On further elution with aqueous ammonium hydroxide (1 M), ninhydrin positive fractions were collected and combined and the solvent was removed in vacuo. Recrystallisation from ethanol/acetone followed by drying gave the desired title compound (12) as a pale yellow oil (2.82 g, 95%): $^1$H-NMR (300 MHz, CDCl$_3$) $\delta_H$ 0.88 (3H, 2×d, J=6.9 and 7.5 Hz, PCH$_2$CH$_2$CH$_2$CH$_3$),0.91 (3H, 2×d, J=7.2 and 7.2 Hz, PCH$_2$CH$_2$CH$_2$CH$_3$), 1.21–1.98 (9H, m, POCH$_2$CH$_3$, PCH$_2$CH$_2$CH$_2$CH$_3$, PCH$_2$CH$_2$CH$_2$CH$_3$, PCH$_2$CH$_2$CH$_2$CH$_3$), 2.38–2.71 (4H, m, C(4)—H, C(4)—H', C(5)—H and C(5)—H'), 3.87–4.31 (5H, m, POCH$_2$CH$_3$, C(3)—NH$_2$, C(3)—H), 6.51 (1H, d, J=9.6 Hz, C(2)—H); $^{13}$C-NMR (75 MHz, CDCl$_3$) $\delta_C$ 13.43 (s, PCH$_2$CH$_2$CH$_2$CH$_3$),16.39 and 16.47 (d, $^3J_{POCC}$=6.00 Hz, POCH$_2$CH$_3$), 23.41 and 23.46 (2×d, $^2J_{PC}$=3.38 and 3.75 Hz, PCH$_2$CH$_2$CH$_2$CH$_3$), 23.63 and 23.84 (d, $^3J_{PC}$=15.90 Hz, PCH$_2$CH$_2$CH$_2$CH$_3$),27.15 and 28.47 (2×d, J$_{PC}$=99.0 and 99.0 Hz, PCH$_2$CH$_2$CH$_2$CH$_3$), 31.93 and 32.09 (2×d, $^3J_{PC}$=11.63 and 11.70 Hz, C(4)), 34.93 and 35.04 (2×d, $^2J_{PC}$=8.25 and 8.55 Hz, C(5)), 58.86 and 59.09 (2×d, $^3J_{PC}$=17.03 and 17.33 Hz, C(3)), 60.11 and 60.19 (d, $^2J_{POC}$=6.23 Hz, POCH$_2$CH$_3$), 135.63 and 137.72 (d, J$_{PC}$=156.75 Hz, C(1)), 150.47 and 150.66 (2×d, $^2J_{PC}$=13.88 and 13.95 Hz, C(2)); $^{31}$P-NMR (121 MHz, CDCl$_3$) $\delta_P$ 43.18 and 43.28; MS (CI, CH$_4$) m/z 232.0 (16%) (MH$^+$), 215.1 (100), 446.0 (18), 260.2 (14).

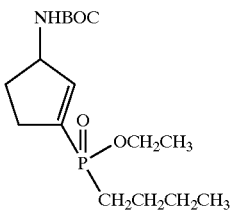

Synthesis of (±)-ethyl [3-(t-butyloxycarbonyl)aminocyclopentenyl]butylphosphinate (13)

To a solution of (±)-ethyl (3-aminocyclopentenyl)butylphosphinate (12) (2.67 g, 11.5 mmol) in aqueous sodium hydroxide (538 mg, 13.5 mmol in 30 cm$^3$) was added di-t-butyl dicarbonate (2.94 g, 13.5 mmol). The reaction mixture was stirred at room temperature for 16 hours after which time the aqueous solution was extracted with DCM (2×30 cm$^3$). The crude product was purified by short column vacuum chromatography on silica gel (15% ethanol/ethyl acetate) to yield the desired title compound (13) as a colourless oil (3.18 g, 83%): $^1$H-NMR (300 MHz, CDCl$_3$) $\delta_H$ 0.91 (3H, 2×d, J=6.0 and 6.3 Hz, PCH$_2$CH$_2$CH$_2$CH$_3$),1.20–1.84 (18H, m, POCH$_2$CH$_3$, PCH$_2$CH$_2$CH$_2$CH$_3$, PCH$_2$CH$_2$CH$_2$CH$_3$, PCH$_2$CH$_2$CH$_2$CH$_3$, C(CH$_3$)$_3$), 2.39–2.73 (4H, m, C(4)—H, C(4)—H', C(5)—H and C(5)—H'), 3.87–4.18 (2H, m, POCH$_2$CH$_3$,), 4.58 (1H, m, C(3)—NH), 4.85 (1H, m, C(3)—H), 6.48 (1H, m, C(2)—H); $^{13}$C-NMR (75 MHz, CDCl$_3$) $\delta_C$13.53 (s, PCH$_2$CH$_2$CH$_2$CH$_3$),16.52 and 16.60 (d, $^3J_{POCC}$=6.23 Hz, POCH$_2$CH$_3$), 23.52 and 23.56 (d, $^2J_{PC}$=3.68 Hz, PCH$_2$CH$_2$CH$_2$CH$_3$), 23.74 and 23.95 (d, $^3J_{PC}$=15.98 Hz, PCH$_2$CH$_2$CH$_2$CH$_3$), 27.34 and 28.66 (2×d, J$_{PC}$=99.01 and 99.30 Hz, PCH$_2$CH$_2$CH$_2$CH$_3$), 28.36 (s, C(CH$_3$)$_3$), 31.84 and 31.99 (2×d, $^3J_{PC}$=11.10 and 11.63 Hz, C(4)), 32.42 and 32.53 (d, $^2J_{PC}$=8.25 Hz, C(5)), 57.82 (m, C(CH$_3$)$_3$), 57.82 and 58.29 (d, $^3J_{PC}$=35.63 Hz, C(3)), 60.29 and 60.38 (d, $^2J_{POC}$=6.53 Hz, POCH$_2$CH$_3$), 137.95 and 139.54 (d, J$_{PC}$=119.25 Hz, C(1)), 145.97 and 146.19 (2×d, $^2J_{PC}$=16.20 and 16.50 Hz, C(2)), 155.06 (s, C=O); $^{31}$P-NMR (121 MHz, CDCl$_3$) $\delta_P$ 42.53 and 42.65; MS (CI, CH$_4$) m/z 332.0 (32%) (MH$^+$), 276.1 (100), 215.1 (25), 360.2 (24).

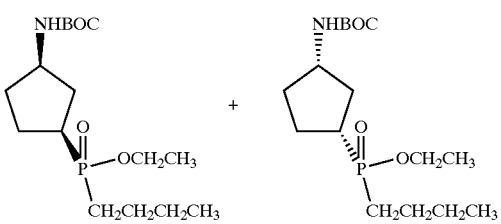

Synthesis of (±)-cis-ethyl [3-(t-butyloxycarbonyl)aminocyclopentanyl]butyl-phosphinate (14)

A solution of (±)-ethyl [3-(t-butyloxycarbonyl)aminocyclopentenyl]butylphosphinate (13) (2.95 g, 8.90 mmol) in methanol (30 cm$^3$) was hydrogenated over platinum oxide (50 mg) at 40 psi for 3 hours. The catalyst was removed by filtration through celite and then washed with methanol (3×30 cm$^3$). The solvent was removed in vacuo to yield the desired title compound (14) in quantitative yield (>90% cis isomer by NMR spectroscopy) as a colourless oil, which was used in the next step without further purification (2.14 g, 72%) (data for cis isomer only is reported):

$^1$H-NMR (300 MHz, CDCl$_3$) $\delta_H$ 0.93 (3H, 2×d, J=6.9 and 7.2 Hz, PCH$_2$CH$_2$CH$_2$CH$_3$),1.21–2.32 (25H, m, C(1)—H, C(2)—H, C(2)—H', C(4)—H, C(4)—H', C(5)—H and C(5)—H', POCH$_2$CH$_3$, PCH$_2$CH$_2$CH$_2$CH$_3$, PCH$_2$CH$_2$CH$_2$CH$_3$, PCH$_2$CH$_2$CH$_2$CH$_3$, C(CH$_3$)$_3$), 4.13 (4H, m, OCH$_2$CH$_3$, C(3)—NH, C(3)—H); $^{13}$C-NMR (75 MHz, CDCl$_3$) $\delta_C$13.49 (s, PCH$_2$CH$_2$CH$_2$CH$_3$), 16.65 (d, $^3J_{POCC}$=3.98 Hz, POCH$_2$CH$_3$), 23.61 (s, C(5)), 23.85 (s, PCH$_2$CH$_2$CH$_2$CH$_3$), 23.88 and 24.04 (d, $^3J_{PC}$=12.53 Hz, PCH$_2$CH$_2$CH$_2$CH$_3$),26.34 and 27.50 (2×d, J$_{PC}$=87.08 and 87.38 Hz, PCH$_2$CH$_2$CH$_2$CH$_3$),28.38 (s, C(CH$_3$)$_3$), 33.02 (s, C(2)), 33.50 and 33.63 (2×d, $^3J_{PC}$=9.08 and 9.98 Hz, C(4)), 34.24 and 35.50 (2×d, J$_{PC}$=94.43 and 94.73 Hz, C(1)), 52.25 (m, C(CH$_3$)$_3$), 60.45 and 60.54 (d, $^2J_{POC}$=6.83 Hz, POCH$_2$CH$_3$), 78.79 and 79.11 (d, $^3J_{PC}$=24.15 Hz, C(3)), 155.42 (s, C=O); 31P-NMR (121 MHz, CDCl$_3$) $\delta_P$ 59.85 and 60.99; MS (CI, CH$_4$) m/z 334.0 (12%) (MH$^+$), 234.2 (100), 278.2 (23), 362.2 (16).

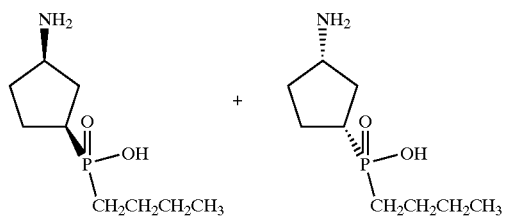

Synthesis of (±)-cis-(3-aminocyclopentanyl)butylphosphinic acid (15)

A solution of (±)-cis-ethyl [3-(t-butyloxycarbonyl)aminocyclopentanyl]butylphosphinate (14) (1.07 g, 3.21 mmol) was dissolved in aqueous HCl (6 M, 40 cm$^3$) and the solution heated at reflux for 30 hours. After cooling, the solution was evaporated to dryness under reduced pressure. The residue was dissolved in water (10 cm$^3$) and applied to an ion exchange column (Dowex 50, H$^+$). The column was eluted with water until the eluate was colourless and the pH 7. On further elution with aqueous pyridine (1 M), ninhydrin positive fractions were collected and the solvent removed in vacuo. Residual traces of pyridine were removed by repeatedly redissolving the compound in water (20 cm$^3$) and re-evaporating (3 times). Recrystallisation from ethanol/acetone followed by drying gave the desired title compound (15) as an off white solid (450 mg, 68%, m.p. (dec.) 180–183° C.): $^1$H-NMR (300 MHz, D$_2$O) $\delta_H$ 0.68 (3H, 2×d, J=6.9 and 7.2 Hz, PCH$_2$CH$_2$CH$_2$CH$_3$),1.02–2.43 (13H, m, C(1)—H, C(2)—H, C(2)—H', C(4)—H, C(4)—H', C(5)—H and C(5)—H', PCH$_2$CH$_2$CH$_2$CH$_3$, PCH$_2$CH$_2$CH$_2$CH$_3$, PCH$_2$CH$_2$CH$_2$CH$_3$),3.56 (1H, m, C(3)—H); $^{13}$C-NMR (75 MHz, D$_2$O) $\delta_C$ 13.46 (s, PCH$_2$CH$_2$CH$_2$CH$_3$), 24.11 and 24.31 (d, $^3J_{PC}$=15.17 Hz, PCH$_2$CH$_2$CH$_2$CH$_3$), 24.31 (s, C(5)), 24.53 and 24.56 (d, $^2J_{PC}$=2.87 Hz, PCH$_2$CH$_2$CH$_2$CH$_3$), 27.96 and 29.17 (d, J$_{PC}$=91.32 Hz, PCH$_2$CH$_2$CH$_2$CH$_3$),31.12 and 31.20 (d, $^2J_{PC}$=6.3 Hz, C(2)), 31.95 (s, C(4)), 36.14 and 37.38 (d, J$_{PC}$=93.33 Hz, C(1)), 52.97 and 52.88 (d, $^3J_{PC}$=7.15 Hz, C(3)); $^{31}$P-NMR (121MHz, D$_2$O) $\delta_P$ 50.74; MS (ESI) m/z 205.9 (37%) (MH$^+$), 411.3 (100), 484.3 (14), 102.4 (12).

Pharmacology

Background to Molecular Biology

Electrophysiology studies involve the use of molecular biology. This is where a specific gene of interest, such as a gene that codes for a receptor or an ion channel, is inserted into a plasmid. For example, ρ1 GABA$_C$ receptor subunit subcloned in ρ1 cDNA 1.1 and is linearised using the restriction enzyme XbaI. Following this, the mRNA is then prepared from the linearised ρ1 subunit using T7 polymerase. This genetic material is then injected into the *Xenopus laevis* oocytes and incubated for 2 to 9 days, to allow for the process of translation to occur. After this process the *Xenopus laevis* oocytes show expression of the receptor and ion channel assembly on the cell surface. The activity and selectivity of (±)-cis- and (±)-trans-3-ACPBPA for the cloned GABA receptors (A, B and C) in the *Xenopus laevis* oocytes are then determined using the two-electrode voltage clamp methods.

*Xenopus laevis* Oocytes

The *Xenopus laevis* oocytes were chosen as the expression system for the study of (±)-cis-and (±)-trans-3-ACPBPA at GABA (A, B and C) receptors. These cells are an appropriate expression system since they are inexpensive, reliable, and robust and most importantly do not express endogenous GABA receptors (Chebib, 2001). Although, these cells have no endogenous GABA receptors, they still contain the required cellular machinery to produce receptors on the cell surface with pharmacological profiles similar to that observed in vivo.

Harvesting *Xenopus* Oocytes

Female *Xenopus laevis* frogs were anaesthetised with tricaine (850 mg/500 mL) and a lobe of their ovaries surgically removed. The lobes were thoroughly washed with oocyte releasing buffer (OR-2) solution (82.5 mM NaCl, 2 mM KCl, 1 mM $MgCl_2.6H_2O$, 5 mM HEPES (hemi-Na salt), pH 7.5) and subsequently incubated with collagenase A (2 mg/mL in OR-2; Boehringer Mannheim, Germany) for 2 hours to separate the oocytes from connective tissue and follicular cells. Stage V–VI oocytes were collected and stored in Frog Ringer (ND96) wash solution (96 mM NaCl, 2 mM KCl, 1 mM $MgCl_2.6H_{20}$, 1.8 mM $CaCl_2.2H_2O$, 5 mM HEPES (hemi-Na salt), pH 7.5) supplemented with 2.5 mM sodium pyruvate, 0.5 mM theophylline, and 50 μg/mL gentamicin.

Expression of mRNA in *Xenopus* Oocytes

Micropipettes were prepared by the microprocessor-controlled vertical pipette puller (World Precision Instruments) and bevelled to a tip diameter of 10–20 μm. The micropipettes were filled with mineral oil to ensure the mRNA solution would be drawn up into the micropipette under negative pressure. A Nanoject injector (World Precision Instruments) was used to deliver $GABA_A$, $GABA_B$ or $GABA_C$ mRNA (50 nL) into the cytoplasm of the *Xenopus* oocytes. After injection with the appropriate mRNA, the oocytes were placed in a storage solution of ND96 wash solution supplemented with 2.5 mM sodium pyruvate, 0.5 mM theophylline and gentamicin (50 μg/mL) and stored on a slow speed rotator in an 18° C. controlled temperature incubator (Contherm, Petone, NZ). The storage solution was changed daily (or twice daily) and dead or unhealthy oocytes were removed to prolong the health of the remaining cells.

Two-Electrode Voltage Clamp Methods

Two-electrode voltage clamp electrophysiology is the most commonly implemented method for recording from oocytes. This method involves the use of two electrodes, one of which injects the current into the cell and the other to record the membrane potential of the cell(Chebib, 2001). This technique measures $GABA_A$ and $GABA_C$ receptor activation, which is a result of the chloride ions moving from inside to the outside of the cell via the receptor channel when clamped at $-60$ $mV^3$. The $GABA_B$ receptor activation is measured as the inwardly rectifying potassium ion conductance through coexpressed GIRKs 1 and 4 when clamped at $-60$ $mV^1$. When the GABA receptors are not activated but blocked (for example, by antagonists) there is no ion conductances measured for each of these GABA receptors and thus the reduction of an electrophysiological reading is noted.

Electrophysiological Recording from Expressed GABA Receptors in *Xenopus* Oocytes Prior to recording, 100 mM stock solutions of (±)-cis- and (±)-trans-3-ACPBPA were prepared using autoclaved Milli-Q water and stored at $-20°$ C. (to prevent the degradation of the synthetic compounds). At the time the experiments were to be recorded, the stock solutions were diluted with ND96 wash solution for testing on $GABA_A$ and $GABA_C$ receptors or 45 mM K$^+$ solution (45 mM NaCl, 45 mM KCl, 1 mM $MgCl_2.6H_2O$, 1.8 mM $CaCl_2.2H_2O$, 5 mM HEPES (hemi-Na salt), pH 7.5 at 25° C.) for testing on $GABA_B$ receptors.

After 2 to 9 days of incubation, receptor activity using two-electrode voltage clamp recordings were acquired by means of a Geneclamp 500 amplifier (Axon Instruments Inc., Foster City, Calif., USA), a MacLab 2e recorder (AD Instruments, Sydney, Australia) and Chart™ v.3.6.3 for Macintosh (AD Instruments) to digitise the current and voltage signals.

The recording microelectrodes were prepared from borosilicate glass capillaries (1.2 mm i.d.×0.94 mm o.d.; Clark Electromedical Instruments, Pangbourne, UK) using a micropipette puller (World Precision Instruments). The microelectrodes (tip resistances 0.5–1.5 MΩ) were filled with 3 M potassium chloride and a microscope was used to direct the insertion of these microelectrodes into the oocyte positioned in the cell bath. The membrane potential of the oocyte was then voltage-clamped at $-60$ mV.

Recording at $GABA_B$ Receptors

The expression of $GABA_B$ receptors was primarily investigated by superfusing the cell bath with ND96 wash solution under gravity at a flow rate of approximately 5 mL/min. The superfusate was then switched to a 45 mM K$^+$ solution and then a solution of GABA in 45 mM K$^+$ was applied.

For subsequent investigation, the cell bath was switched to a 45 mM K$^+$ solution and then briefly switched to 45 mM K$^+$ solutions containing either other GABA concentrations or the desired drugs for testing with and without the presence of GABA.

Recording at $GABA_A$ and $GABA_C$ Receptors

For investigation of $GABA_A$ and $GABA_C$ receptors, the cell bath was continuously superfused with ND96 wash solution, and then for a moment a solution of GABA in ND96 was applied. The superfusate was then switched back to the ND96 wash solution and then momentarily switched to ND96 solutions containing either other GABA concentrations or the desired drugs for testing with and without the presence of GABA.

Generation of Dose-Response Curves

Before recording, the degree of receptor expression was determined by applying a maximal dose of GABA to the clamped oocytes. Oocytes with an adequate level of receptor expression (with maximal currents (I)≧50 nA) were used for subsequent recording. To test the agonist activity of GABA at the receptor, increasing concentrations of GABA solutions (0.1, 0.3, 0.6, 1.0, 3.0, 6.0, 10.0, 30.0, 100.0 and 300.0 μM) were applied to the bath until a maximal current for GABA was achieved. From these results recorded, dose-response relationships could then be produced. For antagonist activity, varying GABA concentrations were co-applied with a fixed concentration of the antagonist, (±)-cis-ACPBPA (40 μM) or (±)-trans-3-ACPBPA (30 μM), to generate a dose-response relationship for comparison to a GABA dose-response on the same cell. Oocytes were washed for 3–4 minutes between applications of drug doses to ensure for receptor recovery. These experiments were carried out on a minimum of 3–4 oocytes, harvested from different frogs (for both (±)-cis- and (±)-trans-3-ACPBPA at the different GABA receptors) to ensure for the statistical significance of the results recorded.

Analysis of Electrophysiological Data

The current generated by (±)-cis- and (±)-trans-3-ACPBPA on the expressed GABA receptors was measured and standardised to the current recorded at each cell for the maximum dose of GABA. The Kaleidograph™ v.2.1.3 (Abelbeck Software) program was implemented to plot the proportion of the maximum response produced by each drug as a function of the GABA concentration applied. The estimated antagonist binding dissociation constant (estimated KB) was calculated using the following equation shown below:

$$\text{Estimated } K_B = [Ant]/((\{A\}/\{A^*\})-1)$$

Where [Ant] is the concentration of the antagonist, $\{A\}$ is the $EC_{50}$ of the agonist in the presence of the antagonist, $\{A^*\}$ is the $EC_{50}$ of the agonist in the absence of the antagonist.

Results

Synthesis

The hydrolysis of the phosphinic ester resulted in the free phosphinic acid moiety in (±)-cis- and (±)-trans-3-ACPBPA. The phosphorus atom in the phosphinic acid moiety is thus no longer chiral in nature, but achiral because both the oxygen atoms of the phosphinic acid are equivalent due to delocalisation. Thus the presence of diastereoisomers associated with the chirality of the phosphorus atom (in the phosphinic ester) is therefore no longer evident in the spectra of (±)-cis- and (±)-trans-3-ACPBPA. Hence the duplication of the peaks in the NMR spectra are clearly evident for the intermediate compounds but not for (±)-cis- and (±)-trans-3-ACPBPA. Nevertheless, the spectra are still complex due to the phosphorus-hydrogen coupling in the $^1$H-NMR spectra and the phosphorus-carbon coupling in the $^{13}$C-NMR spectra Note, in the $^{31}$P-NMR spectra, the phosphorus atom has been decoupled from the hydrogens and carbon in the compounds.

Figure 1:
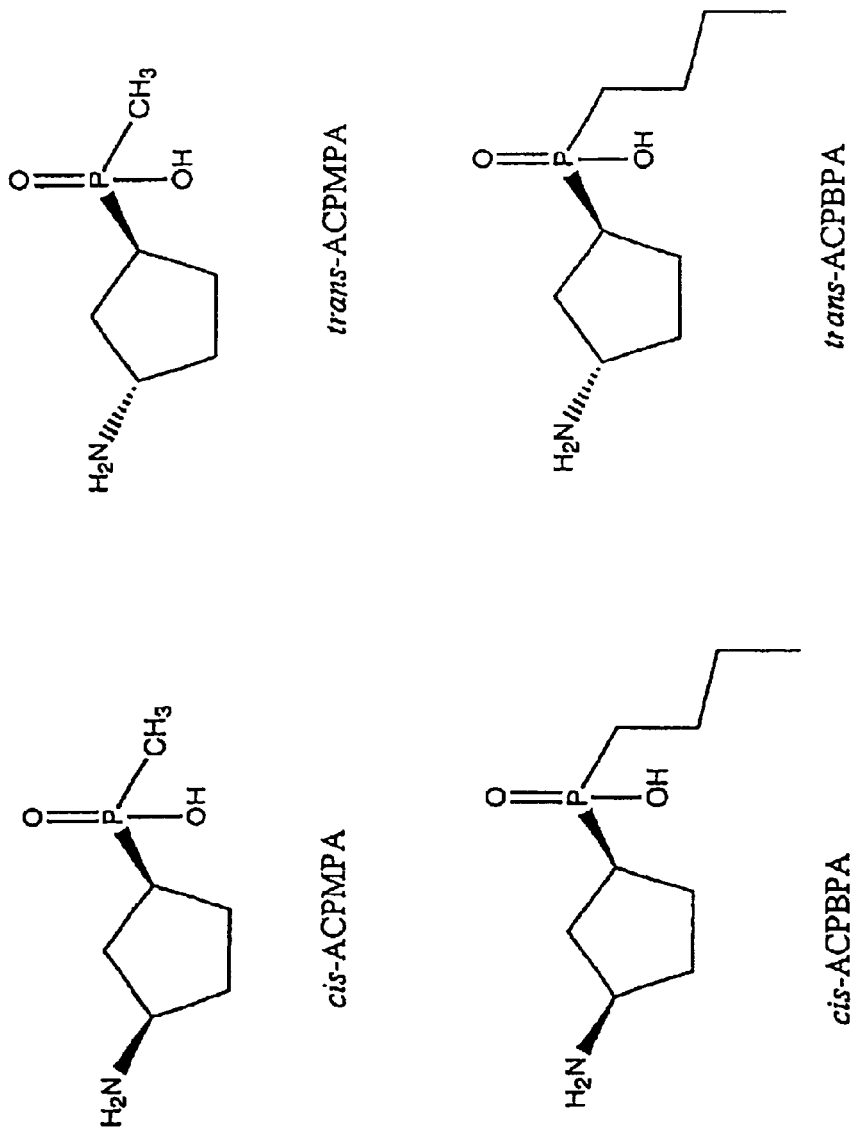
FIG. 1 shows the structure of one isomer of cis-3-(aminocyclopentanyl)methylphosphinic acid (cis-ACPMPA), trans-3-(aminocyclopentanyl)methylphosphinic acid (trans-ACPMPA), cis-3-(aminocyclopentanyl)butylphosphinic acid (cis-ACPBPA) and trans-3-(aminocyclopentanyl)butylphosphinic acid (trans-ACPBPA).
Figure 2:
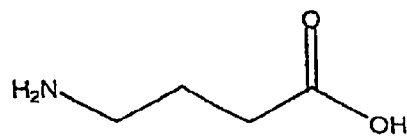
FIG. 2 shows the structures of the compounds GABA, TACA, CACA, CGP27492, 3-APA, CGP35024, TPMA and CGP36742.
Figure 2:
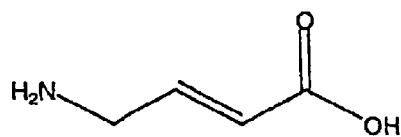
Figure 2:
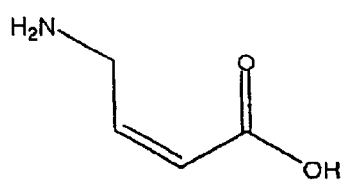
Figure 2:
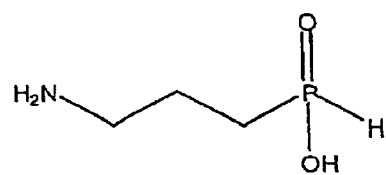
Figure 2:
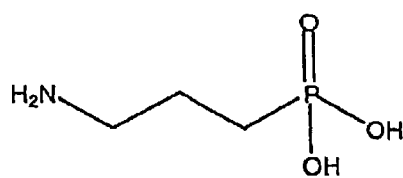
Figure 2:
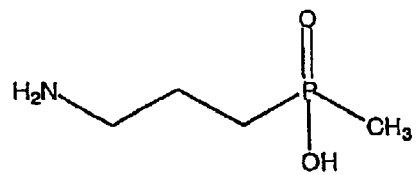
Figure 2:
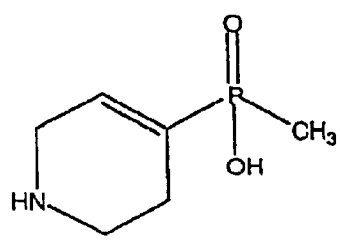
Figure 2:
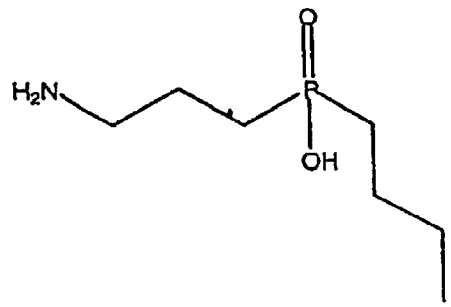
Figure 4:
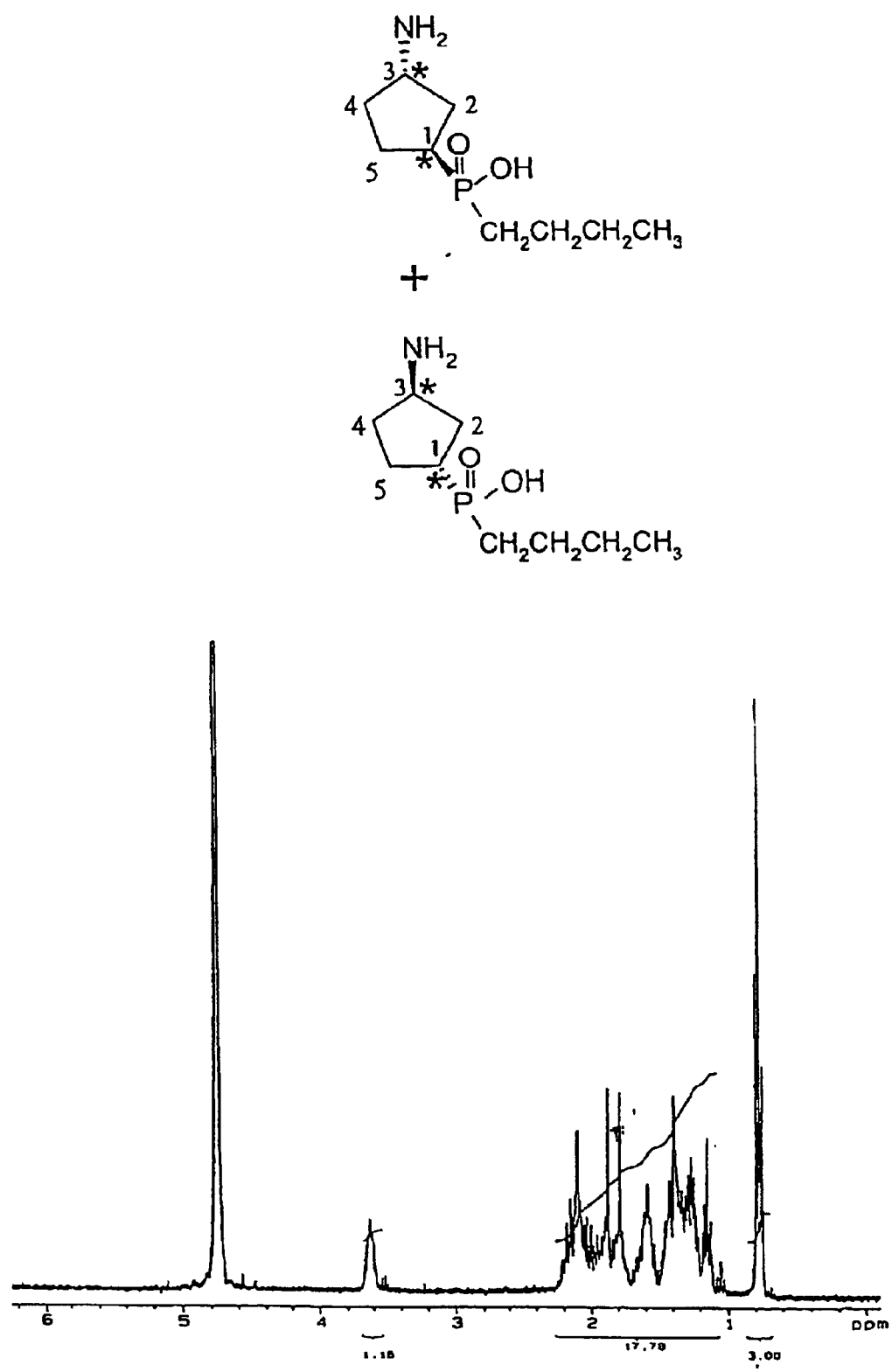
FIG. 4 shows the structure and $^1$H-NMR spectrum of (±)-trans-(3-aminocyclopentanyl)butyl-phosphinic acid (±)-trans-ACPBPA). The spectrum was recorded in deuterated water (D$_2$O) at 300 MHz using a Varian Gemini 300 spectrometer. Chemical shifts ($\delta_H$) are quoted in ppm and referenced externally to TMS at 0 ppm. An asterisk (*) denotes a chiral centre in the compound.

The $^1$H-NMR spectra for (±)-cis- and (±)-trans-3-ACPBPA is shown in FIGS. 3 and 4 respectively. The spectra were recorded in deuterated water ($D_2O$) at 300 MHz using a Varian Gemini 300 spectrometer. Chemical shifts (δp) are quoted in ppm and referenced externally to TMS at 0 ppm.

Interpretation of $^1$H-NMR Spectrum of (±)-cis-3-ACPBPA

The peak at 0.68 ppm is shown as two doublets that overlap each other (hence showing some resemblance of a triplet) with coupling constants of 6.9 and 7.2 Hz. The two doublets is brought about by the three hydrogens of the methyl group in the butyl chain ($PCH_2CH_2CH_2CH_3$) that are coupled only to the two diastereotopic hydrogens of the adjacent methylene carbon. The multiplet spaning across 1.02 to 2.43 ppm is due to twelve hydrogens from both the methylene carbons in the butyl chain ($PCH_2CH_2CH_2CH_3$) as well as those from the cyclopentane ring (C(2)—H, C(2)—H', C(4)—H, C(4)—H', C(5)—H, C(5)—H'), and one hydrogen from the first carbon of the cyclopentane ring (C(1)—H). The multiplet at 3.55 ppm represents the single hydrogen on the third carbon of the cyclopentane ring (C(3)—H). The broad singlet at 4.80 ppm is distinctive of deuterated water. Both the hydrogen from the hydroxyl group of the phosphinic acid moiety (P—OH) and the hydrogens from the amino group (NH2) are found to exchange with deuterated water, producing this characteristic broad peak.

Interpretation of $^1$H-NMR Spectrum of (±)-trans-3-ACPBPA

The triplet at 0.78 ppm represents the three hydrogens of the methyl group in the butyl chain ($PCH_2CH_2CH_2CH_3$), with coupling constants of 7.2 and 7.2 ppm. The multiplet spaning across 1.02 to 2.24 ppm is due to twelve hydrogens from both the methylene carbons in the butyl chain ($PCH_2CH_2CH_2CH_3$) as well as those from the cyclopentane ring (C(2)—H, C(2)—H', C(4)—H, C(4)—H', C(5)—H, C(5)—H'), and one hydrogen from the first carbon of the cyclopentane ring (C(1)—H). The multiplet at 3.6 ppm is characteristic of the single hydrogen on the third carbon of the cyclopentane ring (C(3)—H). The broad singlet at 4.75 ppm is distinctive of deuterated water. Both the hydrogen from the hydroxyl group of the phosphinic acid moiety (P—OH) and the hydrogens from the amino group (NH2) are found to exchange with deuterated water, producing this characteristic broad peak.

Furthermore, the $^1$H-NMR spectra for (±)-cis- and (±)-trans-3-ACPBPA are in actual fact quite similar. However, differentiation can be made with reference to the multiplet corresponding to the single hydrogen associated with the third carbon of the cyclopentane ring (C(3)—H). The multiplet representative of C(3)—H was observed at 3.55 ppm for (±)-cis-3-ACPBPA compared with that shifted to 3.63 ppm for (±)-trans-3-ACPBPA.

Figure 5:
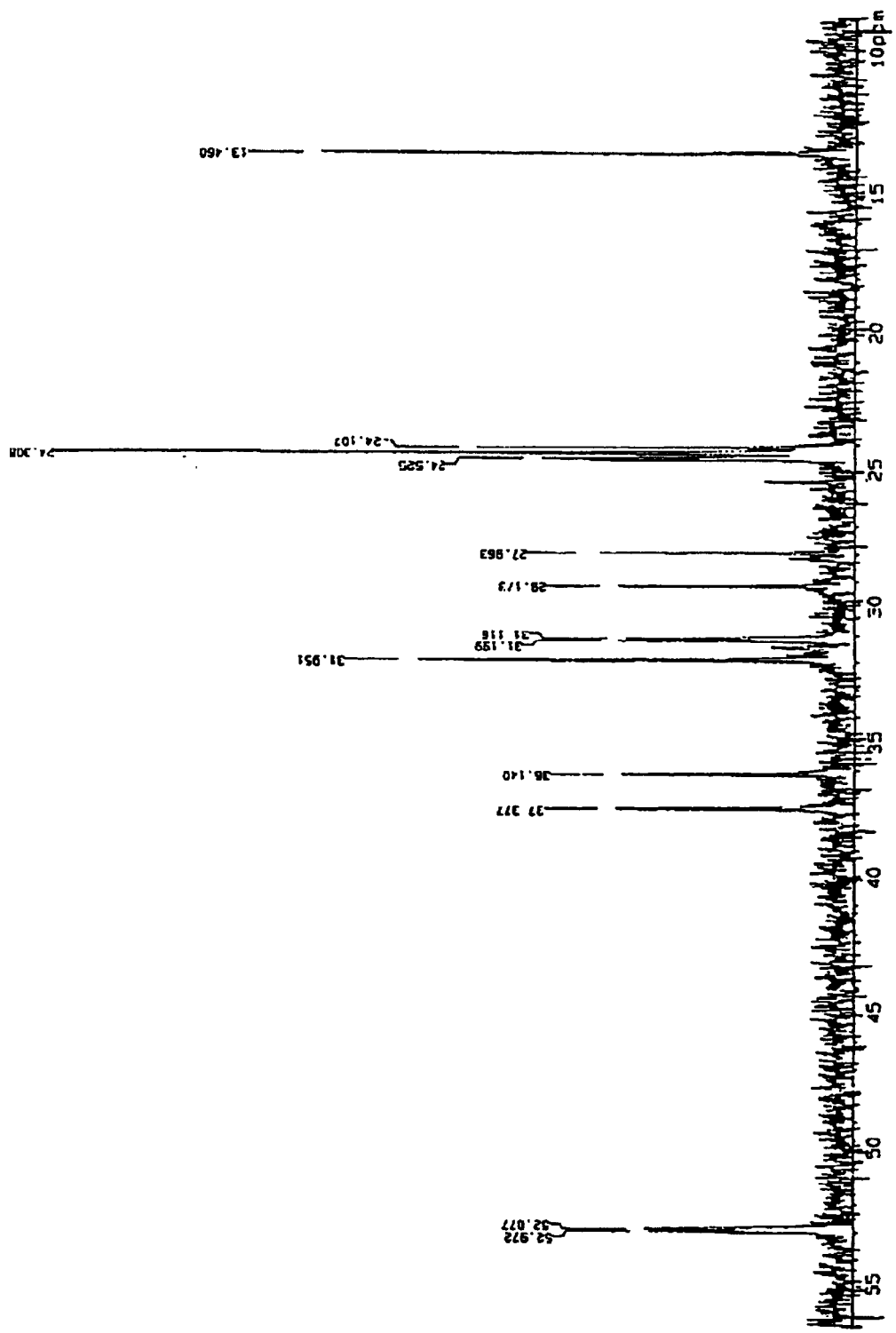
FIG. 5 shows the $^{13}$C-NMR spectrum of ((±)-cis-(3-aminocyclopentanyl)butylphosphinic acid ((±)-cis-ACPBPA). The spectrum was recorded in deuterated water (D$_2$O) at 75 MHz on a Varian Gemini 300 spectrometer. Chemical shifts ($\delta_C$) are quoted in ppm and referenced to CDCl$_3$ AT 77.0 ppm.
Figure 6:
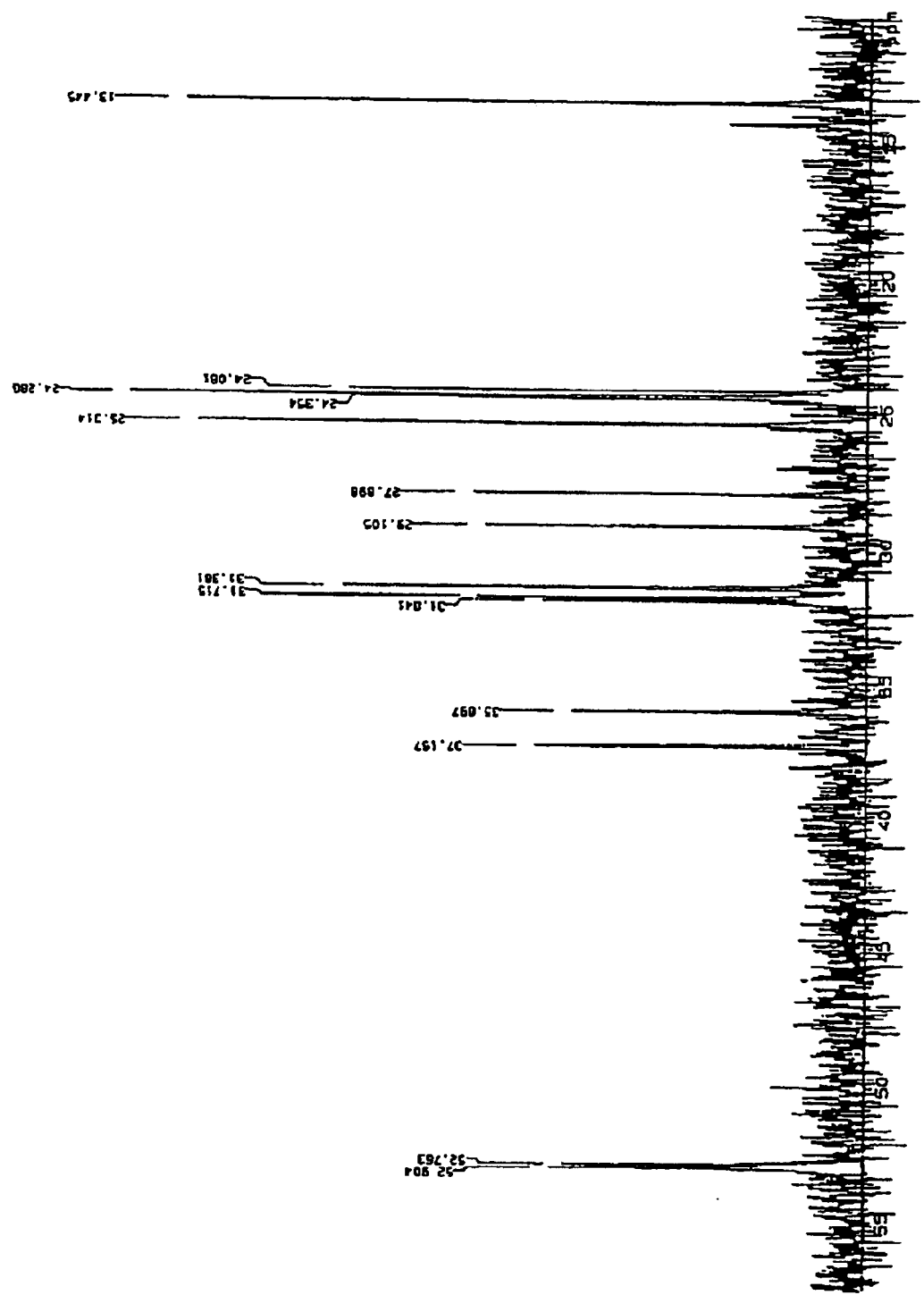
FIG. 6 shows the $^{13}$C-NMR spectrum of (±)-trans-(3-aminocyclopentanyl)butylphosphinic acid ((±)-trans-ACPBPA). The spectrum was recorded in deuterated water (D$_2$O) as 75 MHz on a Varian Gemini 300 spectrometer. Chemical shifts ($\delta_C$) are quoted in ppm and referenced to CDCl$_3$ at 77.0 ppm.

The $^{13}$C-NMR spectra for (±)-cis- and (±)-trans-3-ACPBPA is shown in FIGS. 5 and 6 respectively. The spectra were recorded in deuterated water $D_2O$) at 75 MHz on a Varian Gemini 300 spectrometer. Chemical shifts ($\delta_C$) are quoted in ppm and referenced to $CDCl_3$ at 77.0 ppm.

Interpretation of $^{13}$C-NMR Spectrum of (±)-cis-3-ACPBPA

The singlet at 13.46 ppm is representative of the methyl carbon in the butyl chain ($PCH_2CH_2CH_2CH_3$). The peaks at 24.11 and 24.31 ppm correspond to the third methylene carbon from the phosphorus atom in the butyl chain ($PCH_2CH_2CH_2CH_3$), and are representative of a doublet with a coupling constant of $^3J_{PC}$=15.17 Hz. The singlet at 24.31 ppm is also characteristic of the fifth carbon of the cyclopentane ring (C(5)) with a coupling constant of $^2J_{PC}$=0. The second methylene carbon form the phosphorus atom in the butyl chain ($PCH_2CH_2CH_2CH_3$) is shown as a doublet with a small coupling constant of $^2J_{PC}$=2.87 Hz, at 24.53 and 24.56 ppm. The doublet with a large coupling constant of $J_{PC}$=91.32 Hz, displayed at 27.96 and 29.17 ppm signifies the first methylene carbon in the butyl chain directly bound to the phosphorus atom ($CH_2CH_2CH_2CH_3$). As shown with the butyl chain, a coupling constant through three bonds ($^3J_{PC}$) is smaller than that through one bond ($J_{PC}$) but larger than through two bonds ($^2J_{PC}$). The peaks at 31.12 and 31.20 ppm are due to a doublet with a small coupling constant of $^2J_{PC}$=6.3 Hz, representative of the second carbon of the cyclopentane ring (C(2)). The singlet at 31.95 ppm corresponds to the fourth carbon of the cyclopentane ring (C(4)) with a coupling constant of $^3J_{PC}$=0. The first carbon of the cyclopentane ring (P—C(1)) is characterised by a doublet at 36.14 and 37.38 ppm with a large coupling constant of $J_{PC}$=93.33 Hz. The peaks at 52.97 and 52.88 ppm represent a doublet with a coupling constant of $^3J_{PC}$=7.15 ppm that corresponds to the third carbon of the cyclopentane ring (C(3)). As shown with the cyclopentane ring, a coupling constant through three bonds ($^3J_{PC}$) is smaller than that through one bond ($J_{PC}$) but larger than through two bonds ($^2J_{PC}$).

Interpretation of $^{13}$C-NMR Spectrum of (±)-trans-3-ACPBPA

The singlet at 13.45 ppm is characteristic of the methyl carbon in the butyl side chain (PCH$_2$CH$_2$CH$_2$CH$_3$) The peaks at 24.08 and 24.29 ppm correspond to the third methylene carbon from the phosphorus atom in the butyl side chain (PCH$_2$CH$_2$CH$_2$CH$_3$), and are indicative of a doublet with a coupling constant of $^3J_{PC}$=15.46 Hz. The second methylene carbon form the phosphorus atom in the butyl chain (PCH$_2$CH$_2$CH$_2$CH$_3$) is shown as a doublet with a small coupling constant of $^2J_{PC}$=5.15 Hz, at 24.29 and 24.35 ppm. The singlet at 25.31 ppm is characteristic of the fifth carbon of the cyclopentane ring (C(5)) with a coupling constant of $^2J_{PC}$=0. The doublet with a large coupling constant of $J_{PC}$=91.04 Hz, displayed at 27.90 and 29.11 ppm signifies the first methylene carbon in the butyl chain directly bound to the phosphorus atom (PCH$_2$CH$_2$CH$_2$CH$_3$). As shown with the butyl chain, a coupling constant through three bonds ($^3J_{PC}$) is smaller than that through one bond ($J_{PC}$) but larger than through two bonds ($^2J_{PC}$). The peak at 31.38 ppm is representative of a singlet from the second carbon of the cyclopentane ring (C(2)) with a coupling constant of $^2J_{PC}$=0. The doublet at 31.72 and 31.84 ppm have a coupling constant of $^3J_{PC}$=9.45 Hz, which corresponds to the fourth carbon of the cyclopentane ring (C(4)). The first carbon of the cyclopentane ring (P—C(1)) is characterised by a doublet at 35.90 and 37.16 ppm with a large coupling constant of $J_{PC}$=95.05 Hz. The peaks at 52.76 and 52.90 ppm represent a doublet with a coupling constant of $^3J_{PC}$=10.59 ppm, which corresponds to the third carbon of the cyclopentane ring (C(3)). As shown for the cyclopentane ring, a coupling constant through three bonds ($^3J_{PC}$) is smaller than that through one bond ($J_{PC}$) but larger than through two bonds ($^2J_{PC}$).

Figure 7:
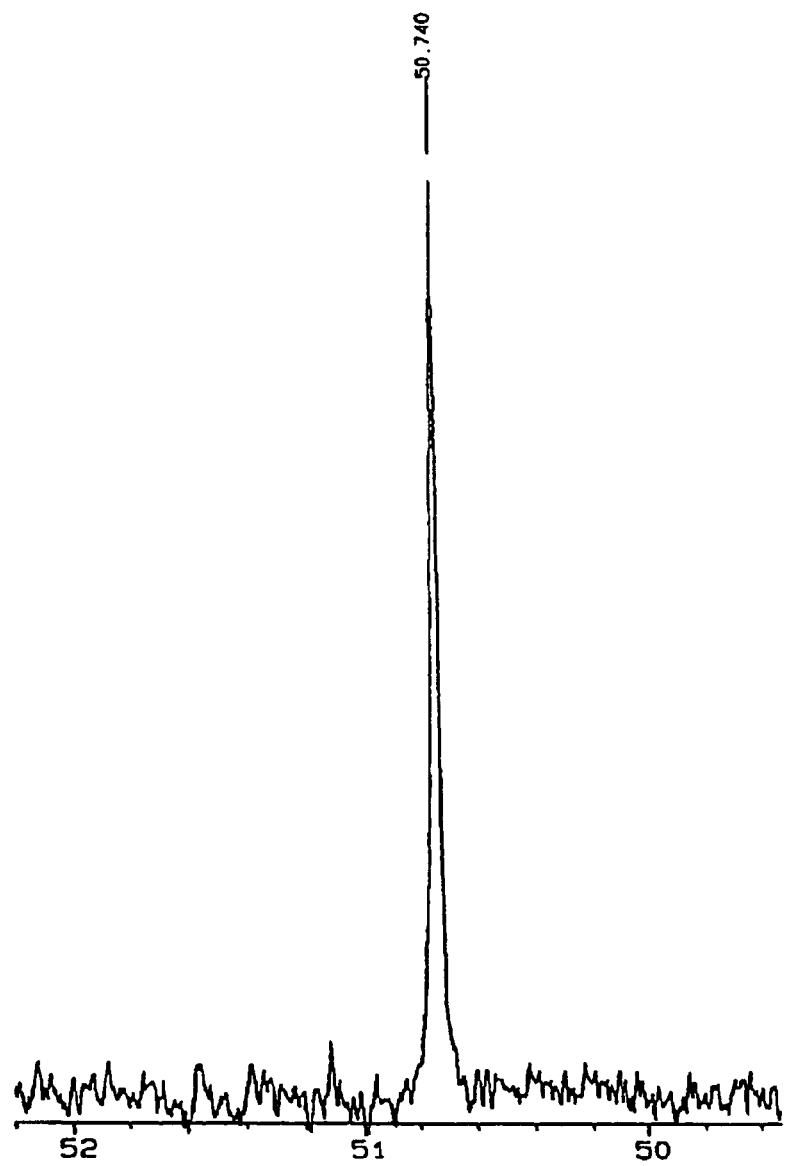
FIG. 7 shows the $^{31}$P-NMR spectrum of (±)-cis-(3-aminocyclopentanyl)butylphosphinic acid ((±)-cis-ACPBPA). The spectrum was recorded in deuterated water (D$_2$O) at 121 MHz on a Varian Gemini 300 spectrometer and referenced externally to 85% H$_3$PO$_4$.
Figure 8:
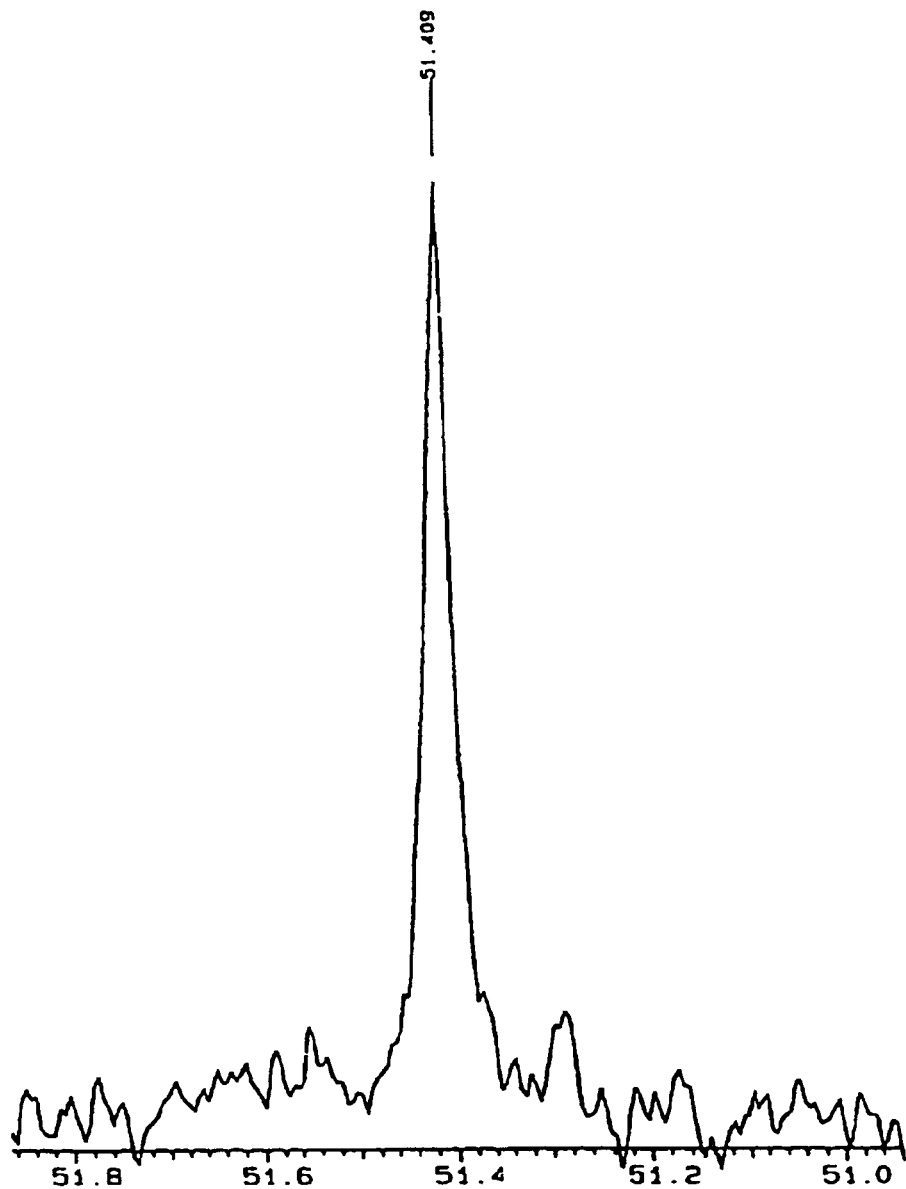
FIG. 8 shows the $^{31}$P-NMR spectrum of (±)-trans-(3-aminocyclopentanyl)butylphosphinic acid ((±)-trans-ACPBPA). The spectrum was recorded in deuterated water (D$_2$O) at 121 MHz on a Varian Gemini 300 spectrometer and referenced externally to 85% H$_3$PO$_4$.

The $^{31}$P-NMR spectra for (±)-cis- and (±)-trans-3-ACPBPA is shown in FIGS. 7 and 8 respectively. The spectra were recorded in deuterated water (D$_2$O) at 121 MHz on a Varian Gemini 300 spectrometer and referenced externally to 85% H$_3$PO$_4$.

Interpretation of 31P-NMR Spectrum of (±)-cis-3-ACPBPA

The singlet at 50.74 ppm represents the phosphorus atom of (±)-cis-3-ACPBPA, decoupled from the hydrogens and carbons in the compound. This singlet is characteristic of the compound adopting an achiral nature. This is where the proton from the phosphinic acid moiety is capable of oscillating between the two oxygen atoms (P—OH and P=O) since their electrons are delocalised equally across each other. Therefore, the diastereoisomers that were originally associated with the chirality of the phosphorus atom in the phosphinic ester, no longer exist in the achiral phosphorus atom of the phosphinic acid.

Interpretation of 31P-NMR Spectrum of (±)-trans-3-ACPBPA

The singlet at 51.41 pm represents the phosphorus atom of (±)-trans-3-ACPBPA, decoupled from the hydrogens and carbons in the compound. As mentioned for the cis compound, this peak is characteristic of the compound adopting an achiral nature. Hence, the phosphorus atom of the phosphinic ester has lost its chirality and the associated diastereoisomers, when the phosphinic ester was cleaved to form the phosphinic acid.

Pharmacology

Expression of GABA$_A$ Receptors

Figure 9:
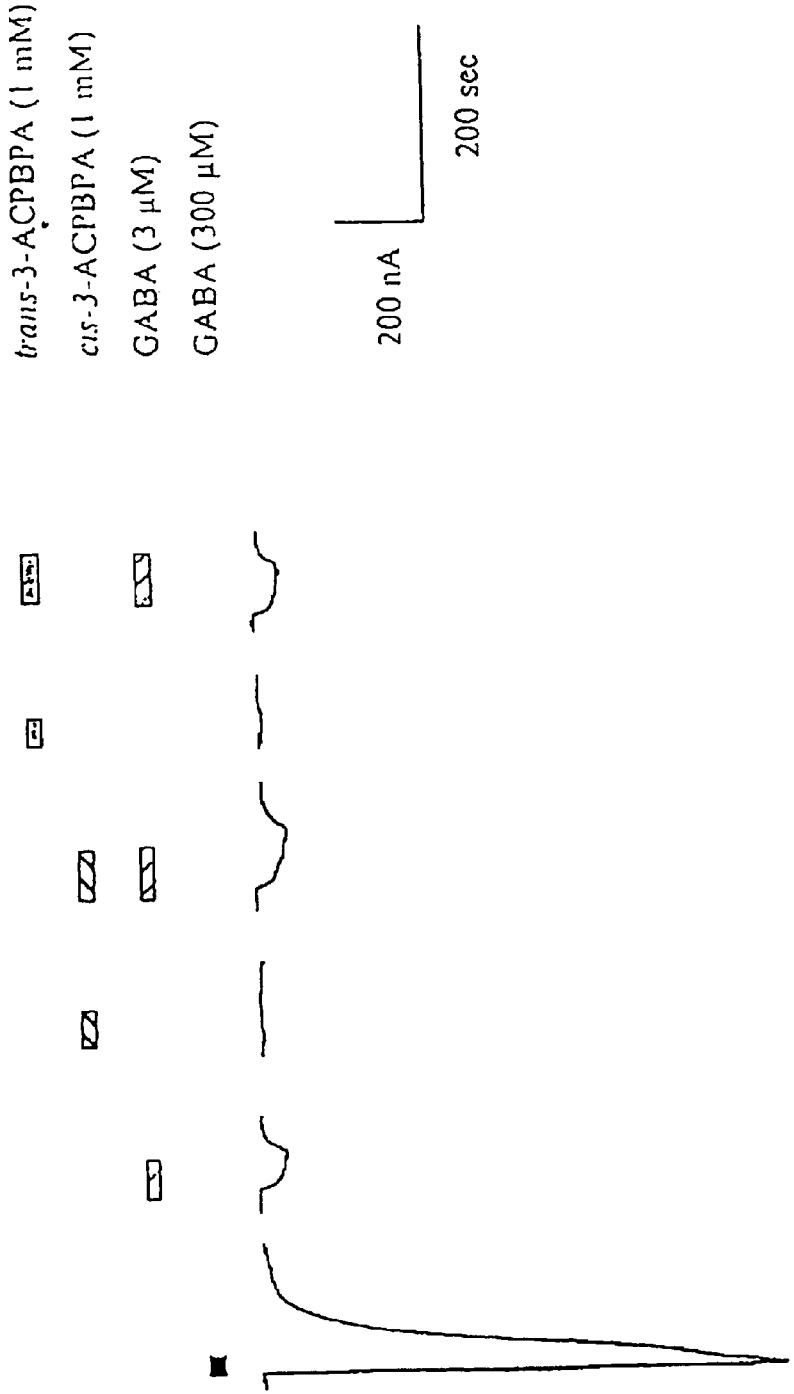
FIG. 9 shows the current responses in the presence of ND96 of GABA$_A$ ($\alpha$2$\beta$2$\gamma$2s) receptors expressed in *Xenopus* oocytes clamped at −60 mV, in the presence of GABA (300 μM) (duration indicated by black filled bar) alone, GABA (3 μM) (duration indicated by lightly hatched bar) alone, cis-3-ACPBPA (1 mM) (duration indicated by heavily hatched bar) alone, cis-3-ACPBPA (1 mM) in combination with GABA (3 μM), trans-3-ACPBPA (1 mM) (duration indicated by grey shaded bar) alone and trans-3-ACPBPA (1 mM) in combination with GABA (3 μM).

As shown in FIG. 9, the cells co-injected with GABA$_A$ (α2), GABA$_A$ (β2), GABA$_A$ (γ2s) mRNA illustrated a response to a solution of a 300 μM (1180 nA) and 3 μM (65 nA) GABA, respectively. Desensitisation of the response to GABA was occasionally observed for the GABA$_A$ (α2β2γ2s) receptor, as illustrated in FIG. 9. The cell was then super-fused with a solution of 1 mM cis-3-ACPBPA, to which no response was detected. The response to 1 mM (±)-cis-3-ACPBPA in the presence of 3 μM GABA (65 nA) resembled that of 3 μM GABA alone, indicating that (±)-cis-3-ACPBPA did not act as an agonist or antagonist at this receptor. Following this, a 1 mM solution of (±)-trans-3-ACPBPA was administered and there was also no detectable response noted. A solution of 1 mM trans-3-ACPBPA in the presence of 3 μM GABA (60 nA) was applied and essentially resembled that of 3 μM GABA alone, indicating that (±)-trans-3-ACPBPA did not act as an agonist or antagonist at this receptor.

Expression of GABA$_B$ Receptors

As shown in FIG. 10(a), cells co-injected with GABA$_B$ (1b), GABA$_B$ (2), GIRK1 and GIRK4 mRNA showed a response to 45 mM K$^+$ solution (125 nA) and further response to an application of 10 μM (140 nA), 3 μM (55 nA) and 1 μM (20 nA) GABA, respectively. The cell was then super-fused with a solution of 300 μM (±)-cis-3-ACPBPA, to which no response was detected. The response to 300 μM (±)-cis-3-ACPBPA in the presence of 1 μl GABA (20 nA) resembled that of 1 μM GABA alone, indicating that (±)-cis-3-ACPBPA did not act as an agonist or antagonist at this receptor. Following this, a 300 μM solution of (trans-3-ACPBPA was administered and there was also no detectable response noted. A solution of 300 μM (±)-trans-3-ACPBPA in the presence of 1 μM GABA (15 nA) was applied and again resembled that of 1 μM GABA alone, indicating that (±)-trans-3-ACPBPA did not act as an agonist or antagonist at this receptor. Furthermore, the cell recovered to their resting potential with the application of a 45 mM K$^+$ solution and ND96 solution, respectively.

As shown in FIG. 10(b), cells co-injected with GABA$_B$ (1a), GABA$_B$ (2), GIRK1 and GIRK4 μM RNA showed a response to the application of 3 μM GABA (405 nA). The cell was then super-fused with a solution of 300 μM (±)-cis-3-ACPBPA, which no response was detected. The response to 300 μM (±)-cis-3-ACPBPA in the presence of 3 μM GABA (405 nA) resembled that of 3 μM GABA alone, indicating that (±)-cis-3-ACPBPA did not act as an agonist or antagonist at this receptor. Following this, a 300 μM solution of (±)-trans-3-ACPBPA was administered and there was also no detectable response noted. A solution of 300 μM (±)-trans-3-ACPBPA in the presence of 3 μM GABA (407 nA) was applied and again resembled that of 3 μM GABA alone, indicating that (±)-trans-3-ACPBPA did not act as an agonist or antagonist at this receptor.

Expression of GABA$_C$ Receptors

As shown in FIG. 11(a), the cells injected with GABA$_C$ (ρ1) mRNA showed a response to the application of 10 μM (142 nA) and 1 μM (105 nA) GABA solution, respectively. The administration of a solution of 100 μM (±)-cis-3-ACPBPA displayed no recordable response, indicating that (±)-cis-3-ACPBPA did not act as an agonist at this receptor. However, the application of 100 μM (±)-cis-3-ACPBPA in the presence of 1 μM GABA (2 nA) resulted with essentially 100% inhibition of the 1 μM GABA response, indicating (±)-cis-3-ACPBPA did act as an antagonist at the ρ1 GABA$_C$ receptor. Following this, a 100 μM solution of (±)-trans-3-ACPBPA was administered and there was also no detectable response noted, indicating that (±)-trans-3-ACPBPA did not act as an agonist at this receptor. While a solution of 100 μM (±)-trans-3-ACPBPA in the presence of 1 μM GABA (34 nA) showed 77% inhibition of the GABA response, indicating (±)-trans-3-ACPBPA did act as an antagonist at the ρ1 GABA$_C$ receptor. Furthermore, the 1 μM GABA response was blocked to a lesser extent than that illustrated by the cis compound on the same receptor. In FIG. 11(b) the cells injected with GABA$_C$ (ρ2) mRNA displayed a response to the application of 100 μM (35 nA) and 1 μM (23 nA) GABA, respectively. The cell was then super-fused with a solution of 100 μM (±)-cis-3-ACPBPA, which displayed no detectable response, indicating that (±)-cis-3-

ACPBPA did not act as an agonist at this receptor. However, the application of 100 μM (±)-cis-3-ACPBPA in the presence of 1 μM GABA (4 nA) resulted with essentially 100% inhibition of the 1 μM GABA response, indicating (±)-cis-3-ACPBPA did act as an antagonist at the ρ2 $GABA_C$ receptor. Subsequent administration of a 100 μM solution of (±)-trans-3-ACPBPA also showed no measurable response, indicating that (±)-trans-3-ACPBPA did not act as an agonist at this receptor. While a solution of 100 μM (±)-trans-3-ACPBPA in the presence of 1 μM GABA (17 nA) displayed 32% inhibition of the GABA response, indicating (±)-trans-3-ACPBPA did act as an antagonist at the ρ2 $GABA_C$ receptor. In addition, the 1 μM GABA response was blocked to a much lesser extent than that illustrated by the cis compound on the same receptor as well as by the trans compound at the ρ1 $GABA_C$ receptor. Note, small currents were occasionally observed for the $GABA_C$ (ρ2) receptor.

In FIG. 11(c) the cells injected with $GABA_C$ (ρ3) mRNA displayed a response to the application of 10 μM (880 nA) GABA solution. The administration of a solution of 100 μM (±)-cis-3-ACPBPA displayed no measurable response, indicating that (±)-cis-3-ACPBPA did not act as an agonist at this receptor. However, the application of 100 μM (±)-cis-3-ACPBPA in the presence of 10 μM GABA (120 nA) resulted with 85% inhibition of the GABA response, indicating (±)-cis-3-ACPBPA did act as an antagonist at the ρ3 $GABA_C$ receptor. Following this, a 100 μM solution of (±)-trans-3-ACPBPA was administered with no visible response noted, indicating that (±)-trans-3-ACPBPA did not act as an agonist at this receptor. While a solution of 100 μM (±)-trans-3-ACPBPA in the presence of 10 μM GABA (455 nA) showed 45% inhibition of the GABA response, indicating (±)-trans-3-ACPBPA did act as an antagonist at the ρ3 $GABA_C$ receptor. Furthermore, the 10 μM GABA response was blocked to a lesser extent than that illustrated by the cis compound on the same receptor. Note that 10 μM GABA was used since a higher concentration of GABA was required in order to activate the $GABA_C$ (ρ3) receptors.

Characterisation of $GABA_C$ (ρ1) Receptors

The effects of the agonist GABA and the antagonists (±)-cis- and (±)-trans-3-ACPBPA at the $GABA_C$ (ρ1) receptor were illustrated via the construction of dose-response curves.

The dose response curve is a function of $I/I_{max}$ versus the GABA concentration (μM) applied. The $I/I_{max}$ is a measure of intrinsic efficacy, which is the portion of the maximum GABA response elicited by each compound. Whereby, I is the degree of GABA response (nA) in the presence of an antagonist and $I_{max}$ is the maximum response (nA) of GABA measured alone.

The dose-response curves in FIGS. 12(a) and (b) show that both (±)-cis- and (±)-trans-3-ACPBPA behave as competitive antagonists over the concentration of the antagonist tested. This was made evident by the parallel shift of the GABA dose-response curves and the maintenance of the maximal response in its presence ($I/I_{max}$ (cis)=0.91±0.02; $I/I_{max}$ (trans)=0.94±0.05). Furthermore, a two-way ANOVA test showed the dose-response curves of GABA in the presence of (±)-cis-3-ACPBPA (40 μM) and GABA in the presence of (±)-trans-3-ACPBPA (30 μM), were both significantly different (p<0.0001) to their respective dose-response curve of GABA alone.

The $EC_{50}$ is described as the concentration that produces half the maximal response. GABA displayed an $EC_{50}$ value of 1.3±0.1 μM at the $GABA_C$ (ρ1) receptor. This $EC_{50}$ value of GABA was shifted to the right to 4.6+0.2 μM and 2.2±0.1 μM in the presence of (±)-cis-3-ACPBPA (40 μM) and (±)-trans-3-ACPBPA (30 μM), respectively.

The estimated antagonist binding constant (estimated $K_B$) is the estimated antagonist binding concentration required to inhibit 50% of the receptors. The estimated $K_B$ values at the ρ1 $GABA_C$ receptor were calculated as 12.5±1.2 μM and 43.8±5.1 μM for (±)-cis-3-ACPBPA and (±)-trans-3-ACPBPA, respectively (refer to Table 1). Therefore, illustrating (±)-cis-3-ACPBPA to be 3.5 times more potent than (±)trans-3-ACPBPA at the ρ1 $GABA_C$ receptor.

In comparison, (±)-cis-3-ACPBPA and (±)-trans-3-ACPBPA at the $GABA_A$ (α2β2γ2s) receptor showed no effect as an agonist or antagonist at a 1 mM concentration (refer to Table 1). Moreover, at the $GABA_B$ (1a,2) and $GABA_B$ (1b,2) receptors, a 300 μM concentration of (±)-cis- and (±)-trans-3-ACPBPA displayed no apparent effect as an agonist or antagonist with an estimated $K_B$>>300 μM (refer to Table 1). Furthermore, a 1 mM concentration of (±)-cis- and (±)-trans-3-ACPBPA at the $GABA_B$ receptor was shown to display a weak antagonist effect (10% inhibition of 1 μM GABA) with an estimated $K_B$>>1000 μM (data not shown).

These results indicate that both (±)-cis- and (±)-trans-3-ACPBPA have greater selectivity for the $GABA_C$ receptors. In particular, (±)-cis-3-ACPBPA was shown to be 100 times more selective for $GABA_C$ over $GABA_B$ or $GABA_A$ receptors.

TABLE 1

The effects of (±)-cis- and (±)-trans-3-ACPBPA at recombinant GABA receptors expressed in Xenopus oocytes. Data are means ± s.e. mean (n = 3–4).

| Compound | $GABA_A$ Receptors α2β2γ2s | $GABA_B$ Receptors (1a, 2) | $GABA_B$ (1b, 2) | $GABA_C$ Receptors ρ1 (μM) |
|---|---|---|---|---|
| (±)-cis-3-ACPBPA | No effect (1 mM) | No effect (300 μM) | No effect (300 μM) | $K_B$ = 12.5 ± 1.2 (100 pM) |
| (±)-trans-3-ACPBPA | No effect (1 mM) | No effect (300 μM) | No effect (300 μM) | $K_B$ = 43.8 ± 5.1 (100 μM) |

The Hill coefficient ($n_H$) is a measure of co-operativity. It can measure the co-operativity of binding of an agonist/antagonist at the designated receptor. Whereby, a $n_H$<1 shows negative co-operativity, a $n_H$>1 demonstrates positive co-operativity and a $n_H$=1 is indicative of no co-operativity. The $n_H$ for GABA alone and GABA in the presence of (±)-cis-3-ACPBPA and (±)-trans-3-ACPBPA were determined to be 1.9±0.3, 2.3±0.2 and 2.2±0.2, respectively. These results tell us that GABA illustrates a positive co-operativity at the ρ1 $GABA_C$ receptor.

In this study, the compounds (±)-cis- and (±)-trans-3-ACPBPA were synthesised and evaluated for their effects at GABA (A, B and C) receptors expressed in Xenopus oocytes using two-electrode voltage clamp methods. The results illustrated that the pharmacological profile of (±)-cis- and (±)-trans-3-ACPBPA varied between the GABA receptors, with the greatest selectivity and activity detected at $GABA_C$ receptors.

At the α2β2γ2s $GABA_A$ receptor, both (±)-cis- and (±)-trans-3-ACPBPA were shown to have no effect as an agonist or an antagonist even when tested at a 1 mM concentration. Similarly, (±)-cis- and (±)-trans-3-ACPBPA (300 μM) at $GABA_B$ (1a,2) and $GABA_B$ (1b,2) receptors showed to have no effect as agonists or antagonists. Increasing the concentration to 1 mM only showed weak effects as antagonists (10% inhibition of 1 μM GABA) at this receptor (data not shown). In contrast, (±)-cis- and (±)-trans-3-ACPBPA were shown to be potent antagonists at all $GABA_C$ receptor subtypes (ρ1, ρ2 and ρ3).

In the above Example, (±)-cis- and (±)-trans-3-ACPBPA were tested and evaluated as the racemic mixture, which is a 50:50 mixture of (±)-cis-3-ACPBPA and (−)-cis-3-ACPBPA and a 50:50 mixture of (±)-trans-3-ACPBPA and (−)-trans-3-ACPBPA.

EXAMPLE 2

Comparison with (±)cis- and (±)-trans-3-(aminocyclopentanyl)methylphosphinic acid In the following Example, (±)-cis- and (±)-trans-3-(aminocyclopentanyl)methylphosphinic acid was prepared and the selectivity for the $GABA_C$ receptor compared with the $GABA_A$ and $GABA_B$ receptors determined.

Synthesis (±)-cis- and (±)-trans-3-(aminocyclopentanyl) methylphosphinic acid was prepared as follows.

3-Iodo-2-cyclopentenone (1) was prepared in high yield as described previously (Piers et al, 1982). Although palladium catalysed coupling reactions have been reported to occur in high yields on a wide variety of substrates, all attempts in our laboratory to carry out the modified Heck reaction of isopropyl methylphosphinate with 3-iodo-2-cyclopentenone (1) or 3-iodo-2-cyclopentenol (2) were unsuccessful. However, in situ protection of the hydroxyl moiety as the trimethylsilyloxy ether followed by reaction under modified Heck conditions allowed the palladium catalysed coupling reaction to proceed smoothly. Addition of ethanol to the reaction mixture at the completion of the reaction facilitated the hydrolysis of the silyl ether affording high yields of isopropyl (3-hydroxycyclopentenyl) methylphosphinate (3) which is the key intermediate in this stereodivergent synthesis (Scheme 1).

Scheme 1

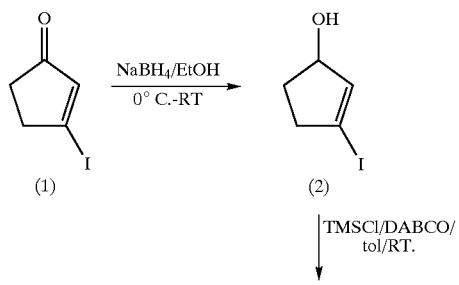

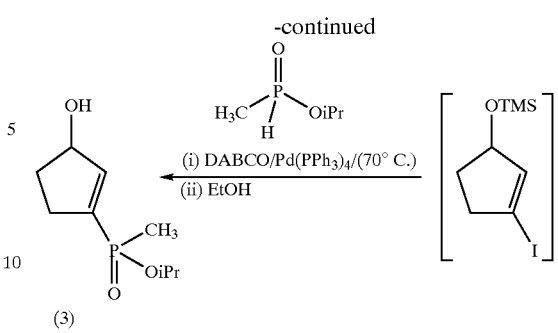

Preliminary experiments on the hydrogenation of isopropyl (3-hydroxycyclopentenyl)methylphosphinate (3) produced a 3:2 mixture of the cis:trans products, as determined by integration of both the P—$CH_3$ methyl and CHOH peaks in the $^1H$ nmr spectrum. This slight inequality in the ratio of the two products prompted us to investigate the effect of the sterically demanding t-butydimethylsilyl group as means to direct the hydrogenation of the double bond. Reaction of isopropyl (3-hydroxycyclopentenyl)methylphosphinate with t-butydimethylsilyl chloride in the presence of triethylamine and DMAP (Scheme 2) gave the TBDMS ether (4) in high yield. [15] Hydrogenation of the TBDMS protected cyclopentenol over palladium on carbon at 10 psi yielded the desired cyclopentane (5) which was determined to be predominantly the cis diastereoisomer. Hydrogenation at higher pressures resulted in some cleaving of the reactive vinylic C—O bond. $^1H$ nmr analysis showed a diastereomeric excess of greater than 9:1 cis:trans. The minor trans isomer could be removed by chromatography on silica gel.

Scheme 2

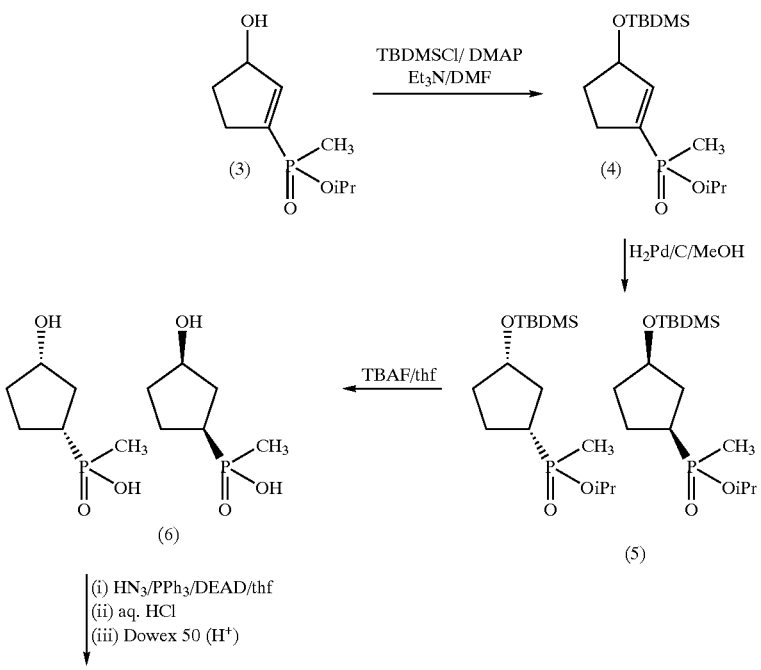

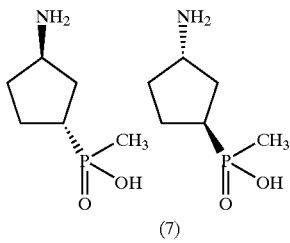

(7)

Deprotection of the (±)-cis-t-butyldimethylsilyl ether (5) by treatment with TBAF afforded the (±)-cis-alcohol (6) in high yield. Reaction of the alcohol under Mitzanobu conditions,[16] resulting in inversion of stereochemistry at the 3-position, yielded the (±)-trans isomers. Acid hydrolysis provided (±)-(trans-3-aminocyclopentanyl) methylphosphinic acid (7) in good yield. This was purified by ion exchange chromatography.

Experimental

Melting points were determined using a Reichert hot-stage melting point apparatus and are uncorrected. $^1$H NMR spectra were recorded at 300 MHz using a Varian Gemini 300 spectrometer. Chemical shifts ($\delta_H$) are quoted in parts per million (ppm), referenced externally to tetramethylsilane (TMS) at 0 ppm. Coupling constants (J) are reported in Hertz. $^{13}$C NMR spectra were recorded at 75 MHz on a

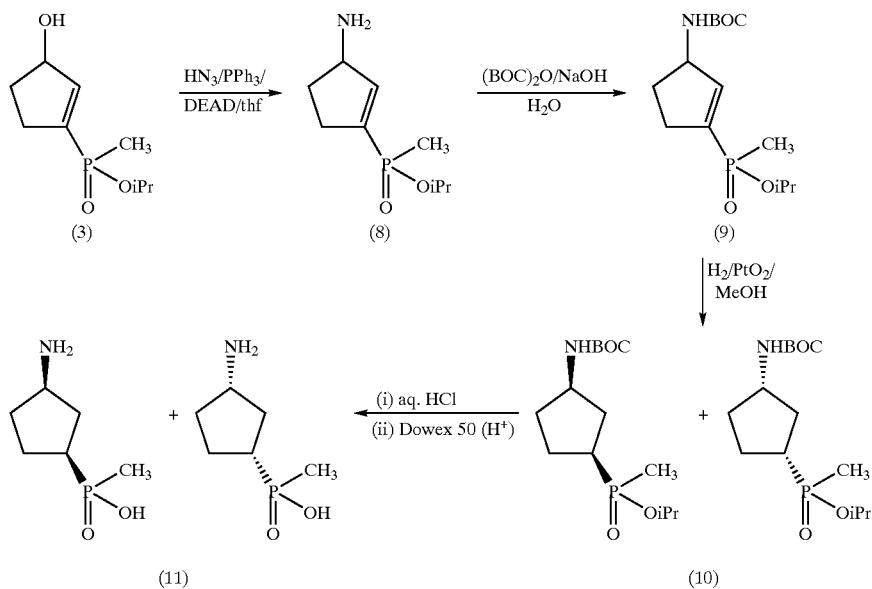

Scheme 3

A related strategy was applied to the synthesis of (±)-(cis-3-aminocyclopentanyl)methylphosphinic acid (Scheme 3). However, in this synthesis, a Mitzanobu reaction was performed at the start of the sequence on isopropyl (±)-(3-hydroxycyclopentenyl)methylphosphinate (3) to yield (±)-isopropyl (3-aminocyclopentenyl)methylphosphinate (8). The amine was then protected as the t-butyloxycarbonylamide (BOC) (9) which provided the steric bulk to direct the approach of the hydrogen. The hydrogenation was carried out over PtO$_2$ at 40 psi affording the (±)-cis-N-butyloxycarbonyl cyclopentane (10) in quantitative yield and a diastereomeric excess of 95:5 cis:trans. The minor diastereoisomer could be separated by silica gel chromatography.

Concurrent deprotection of the phosphinic ester and the N-butyloxycarbonyl amide was carried out in refluxing aqueous HCl. Purification by ion exchange chromatography and recrystallisation yielded the desired (±)-cis-(3-aminocyclopentanyl)methylphosphinic acid (11).

Varian Gemini 300 spectrometer. Chemical shifts ($\delta_C$) are quoted in ppm and referenced to CDCl$_3$ at 77.0 ppm. $^{31}$P Nmr spectra were recorded at 121 MHz on a Varian Gemini 300 spectrometer and referenced externally to 85% H$_3$PO$_4$. Low resolution mass spectra were recorded on a Finnigan/MAT TSQ 7000 LCMS/MS spectrometer; only molecular ions (M$^+$ or MH$^+$) and major peaks are reported with intensities quoted as percentages of the base peak. High resolution mass spectra were recorded on a Micromass QT of II; all samples were run using electrospray ionisation (ESI) with ions measured as protonated molecular ions (MH$^+$). Microanalyses were performed in the Department of Marine Biology at the University of Sydney. Thin layer chromatography (tlc) was performed on Merck aluminium backed plates pre-coated with silica (0.2 mm, 60F$_{254}$) which were developed using one or more of the following agents: UV fluorescence (254 nm), alkaline potassium permanganate solution (0.5% w/v), or ninhydrin (0.2% w/v). Flash vacuum chromatography was performed on silica gel (Merck silica gel 60H, particle size 5–40 µm). Chemicals were purchased from Aldrich at the highest available grade. THF was distilled under nitrogen from sodium-benzophenone.

Unless otherwise noted, the duplication of peaks in the NMR spectra arise from the presence of diastereoisomers associated with the chirality of the phosphorous atom in the phosphinic ester.

Isopropyl (3-hydroxycyclopentenyl)methylphosphinate (3)

To a solution of DABCO (11.8 g, 105 mmol) and 3-iodo-cyclopent-2-enol (5.5 g, 26.3 mmol) in anhydrous toluene (300 cm$^3$) was added trimethylsilyl chloride (3 g, 27.6 mmol). The reaction mixture was stirred at room temperature for 15 min, after which time isopropyl methylphosphinate (4.8 g, 39.4 mmol) and tetrakis(triphenylphosphine) palladium(0) (760 mg, 2.5 mol %) were added. The reaction mixture was heated at 70° C. for 24 h after which time a second portion of tetrakis(triphenylphosphine)palladium(0) (760 mg, 2.5 mol %) was added and heating continued for a further 24 h. The reaction mixture was filtered while still hot and aqueous ethanol (50 cm$^3$) added to the filtrate, which was then concentrated in vacuo. The product was isolated by short column vacuum chromatography on silica gel (15% ethanol/ethyl acetate) to yield the title compound (3) as a slightly coloured oil (3.5 g, 65%): $^1$H NMR (300 MHz, CDCl$_3$) δ 1.25 (3H, t, J=6.4, OCHCH$_3$), 1.327 and 1.333 (3H, 2×d, J=6.2 and 6.2 Hz, OCHCH$_3$), 1.49 and 1.51 (3H, 2×d, J=14.4 and 14.4 Hz, PCH$_3$), 1.76–1.92 (1H, m, C(5)—H), 2.33–2.52 (2H, m, C(5)—H' and C(4)—H), 2.60–2.78 (1H, m, C(4)—H'), 4.55 (1H, m, OCHCH$_3$), 4.95 (1H, m, C(3)—H), 6.57 (1H, m, C(2)—H); $^{13}$C NMR (75.46 MHz, CDCl$_3$) δ 13.8 and 14.0 (PCH$_3$, d, J$_{PC}$=101 and 101 Hz), 23.88 and 23.91 (POCCH$_3$, d, $^3$J$_{POCC}$=4.9 and 4.6 Hz), 24.31 (POCCH$_3$, overlapping d, $^3$J$_{POCC}$=3.4 Hz) 26.89 and 26.91 (C(4), d, $^3$J$_{PC}$=12.8 and 12.5 Hz), 29.27 and 29.35 (C(5), d, $^2$J$_{PC}$=8.8 and 8.6 Hz), 76.94 and 73.65 (POCHCH$_3$, d, $^2$J$_{POC}$=6.0 and 6.3 Hz), 76.94 and 77.18 (C(3), d, $^3$J$_{PC}$=5.0 and 7.5 Hz), 138.11 and 138.22 (C(1), d, J$_{PC}$=126 and 126 Hz), 147.54 (C(2), d, J=10.6 Hz), $^-$P NMR (121 MHz, CDCl$_3$) δ 38.9, 39.0, (ESI) 207.1154 (MH$^+$-C$_9$H$_{20}$O$_3$ requires 207.1150).

Isopropyl [3-(t-butyldimethylsilyloxy)cyclopentenyl]methylphosphinate (4)

A solution of isopropyl (3-hydroxycyclopentenyl)methylphosphinate (3) (3.5 g, 17.2 mmol) in anhydrous DMF (60 cm$^3$) was treated with t-butyldimethylsilyl chloride (2.85 g, 18.9 mmol), triethylamine (3.6 g, 34.3 mmol) and DMAP (250 mg). The reaction mixture was stirred at room temperature for 16 h, after which time the solvent was removed in vacuo. The residue was partitioned between DCM (50 cm$^3$) and water (30 cm$^3$) and the aqueous layer was further extracted with DCM (3×20 cm$^3$). The combined organic layers were washed with water (2×30 cm$^3$) and brine (40 cm$^3$), dried over anhydrous Na$_2$SO$_4$, filtered and the solvent removed under reduced pressure. The crude product was purified by short column vacuum chromatography on silica gel (5% ethanol/ethyl acetate) to yield the title compound (4) as a colourless oil (4.62 g, 85%): $^1$H NMR (300 MHz, CDCl$_3$) δ 0.065 and 0.067 (6H, 2×s), 0.870 and 0.874 (9H, 2×s), 1.22 and 1.24 (3H, 2×d, J=6.3 and 6.3 Hz, OCHCH$_3$), 1.31 and 1.33 (3H, 2×d, J=6.0 and 6.0 Hz, OCHCH$_3$), 1.45 and 1.49 (3H, 2×d, J=14.4 and 14.4 Hz, PCH$_3$), 1.69–1.83 (1H, m, C(5)—H), 2.24–2.46 (2H, m, C(5)—H' and C(4)—H), 2.54–2.68 (1H, m, C(4)—H'), 4.55 (1H, m, OCHCH$_3$), 4.95 (1H, m, C(3)—H), 6.46 (1H, m, C(2)—H), $^{13}$C NMR (75.46 MHz, CDCl$_3$) δ −4.81 and −4.75 (Si(CH$_3$)$_2$, 2×s), 14.0 and 14.19 (PCH$_3$, d, J$_{PC}$=101.3 and 101.8 Hz), 18.07 and 18.10 (SiC(CH$_3$)$_3$, 2×s), 23.90 and 23.96 (POCCH$_3$, 2×d, $^3$J$_{POCC}$=4.8 Hz), 24.43 (POCCH$_3$, overlapping d, $^3$J$_{POCC}$=3.3 Hz), 25.76 (SiC(CH$_3$)$_3$, br. s), 31.34 (C(4), d, $^3$J$_{PC}$=11.5 Hz), 34.42 and 34.55 (C(5), 2×d, $^2$J$_{PC}$=9.5 Hz), 68.95 and 68.99 (POCHCH$_3$, d, $^2$J$_{POC}$=6.5 and 5.9 Hz), 77.98 and 78.24 (C(3), d, $^3$J$_{PC}$=6.9 and 6.7 Hz), 137.78 and 138.08 (C(2), d, J$_{PC}$=125.0 and 125.6 Hz), 147.2 (C(1), d, J=10.7 Hz), $^{31}$P NMR (121 MHz, CDCl$_3$) δ 38.1, 38.5, (ESI) 319.1869 (MH$^+$-C$_{15}$H$_{32}$O$_3$PSi requires 319.1858).

(±)-cis-Isopropyl [3-(t-butyldimethylsilyloxy)cyclopentanyl]methylphosphinate (5)

A solution of isopropyl (3-t-butyldimethylsilyloxycyclopentenyl)methylphosphinate (4) (3.4 g, 10.7 mmol) in methanol (30 cm$^3$) was hydrogenated over palladium on carbon (50 mg) at 40 psi for 3 h. The catalyst was removed by filtration through celite which was washed with methanol (3×30 cm$^3$). The solvent was removed in vacuo to yield the desired product in quantitative yield (>90% cis isomer (5) by nmr spectroscopy). Which was used in the next step without further purification (3.4g, 99%) (data for cis isomer only is reported): $^1$H NMR (300 MHz, CDCl$_3$) δ 0.076 (6H, s), 0.90 (9H, s), 1.32 (6H, d, J=6.1 Hz, OCHCH$_3$), 1.44 (3H, d, J=13.2 Hz, PCH$_3$), 1.63–1.81 (3H, m, C(5)—H, C(5)—H' and C(1)—H), 1.82–1.99 (2H, m, C(2)—H and C(4)—H), 2.09–2.21 (2H, m, C(2)—H' and C(4)—H'), 4.26 (1H, m, C(3)—R), 4.65 (1H, m, OCHCH$_3$), $^{13}$C NMR (75.46 MHz, CDCl$_3$) δ −4.96 (Si(CH$_3$)$_2$, br. s), 11.07 and 12.28 (PCH$_3$, d, J$_{PC}$=91.0 and 91.0 Hz), 17.89 (OSiC(CH$_3$)$_3$, s), 23.99 and 24.01 (C5, s), 24.20 (POC(CH$_3$)$_3$, br. d, J=4.0 Hz), 25.68 (OSiC(CH$_3$)$_3$, br. s) 35.78 and 35.81 (C(2), s), 35.91 and 36.11 (C(4), br. s,), 36.11 and 36.17 (C(1), d, J$_{PC}$=99.6 and 100.7 Hz), 68.25 (POCHCH$_3$, br. d, $^2$J$_{POC}$=6.6 Hz), 73.80 (C(3), d, $^3$J$_{PC}$=11.5 Hz), $^{31}$P NMR (121 MHz, CDCl$_3$) δ 57.9, 58.1, MS (CI) m/z 321 (91%) (MH$^+$), 187 (100), 145 (75), (ESI) 321.2012 (M$^+$-C$_{15}$H$_{34}$O$_3$PSi requires 321.2015).

(±)-cis-Isopropyl (3-hydroxycyclopentanyl)methylphosphinate (6)

To a solution of (±)-cis-isopropyl [3t-butyldimethylsilyloxy)cyclopentanyl]methylphosphinate (5) (3.2 g, 10 mmol) in anhydrous THF (30 cm$^3$) was added tetrabutylammonium fluoride (11 cm$^3$ of a 1 M solution in THF). The reaction mixture was stirred at room temperature for 12 h at which time the solvent was removed in vacuo. The crude product was purified by short column vacuum chromatography on silica gel (15% ethanol/ethyl acetate); earlier fractions contained the trans isomer, later fractions contained the desired cis (6) isomer which was isolated as a colourless oil (1.8 g, 87%): $^1$H NMR (300 MHz, CDCl$_3$) δ 1.28 and 1.31 (6H, d, J=6.3 and 6.3 Hz, OCHCH$_3$), 1.45 (3H, d, J=113.2 Hz, PCH$_3$), 1.61–2.32 (6H, m, C(1)—H, C(2)—H, C(2)—H', C(4)—H, C(4)—H' and C(5)—H), 4.26 (1H, m, C(3)—H), 4.61 (1H, m, OCHCH$_3$), $^{13}$C NMR (75.46 MHz, CDCl$_3$) δ 12.15 and 12.76 (PCH$_3$, d, J$_{PC}$=90.2 and 89.9 Hz), 23.62 (C(5)), 24.20 and 24.24 (POCCH$_3$, 2×d, $^3$J$_{POCC}$=3.3 Hz), 35.24 and 35.29 (C(2, s), 35.81 and 35.89 (C(1), d, J$_{PC}$=97.9 and 98.5 Hz), 35.98 and 36.01 (C(4), d, $^3$J$_{PC}$=7.2 and 7.5 Hz), 69.11 and 69.12 (POCHCH$_3$, d, $^2$J$_{POC}$=6.9 and 6.9 Hz), 72.8 and 73.3 (C(3), d, $^3$J$_{PC}$=4.1 and 4.9 Hz), $^{31}$P NMR (121 MHz, CDCl$_3$) δ 59.4, 59.7, (ESI) 207.1154 (MH$^+$-C$_9$H$_{20}$O$_3$P requires 207.1150).

(±)-trans-(3-Aminocyclopentanyl)methylphosphinic acid (7)

To a stirred solution of (±)-cis-isopropyl (3-hydroxycyclopentanyl)methylphosphinate (6) (1.6 g, 7.8 mmol), DEAD (2.5 cm$^3$, 17.05 mmol) and HN$_3$ (8.2 cm$^3$ of a 1.9 M solution in benzene) in anhydrous THF (70 cm$^3$)

under an atmosphere of $N_2$ at 0° C. was added triphenylphosphine (8.15 g, 31.2 mmol) in small portions over a period of 1 h. The reaction mixture was allowed to warm to room temperature and stirring continued for 12 h. The reaction mixture was then heated to 50° C. for 3 h after which time water (2 cm$^3$) was added and heating continued for a further 2 h. The reaction mixture was cooled to room temperature and the solvent removed in vacuo. The residue was partitioned between aqueous HCl (1 M, 30 cm$^3$) and DCM (30 cm$^3$). The organic layer was separated and further extracted with aqueous HCl (2×30 cm$^3$). The combined aqueous fractions were washed with DCM (2×30 cm$^3$) and concentrated in vacuo. The crude amino ester hydrochloride salt was hydrolysed by refluxing in aqueous HCl (6M) for 30 h after which time the reaction mixture was cooled to room temperature and the aqueous HCl removed under reduced pressure. The crude product was purified by ion exchange chromatography (Dowex 50, H$^+$), eluting first with water until the eluate was colourless and pH 7. On further elution with aqueous pyridine (1M), ninhydrin positive fractions were collected and the solvent removed in vacuo giving an off white foam. Recrystallisation from ethanol/acetone followed by drying gave the desired product (7) (0.68 g, 43%): $^1$H NMR (300 MHz, $D_2O$) δ 1.17 (3H, d, J=12.3 Hz, $PCH_3$), 1.52–2.06 (7H, m, C(1)—H, C(2)—H, C(2)—H', C(4)—H, C(4)—H', C(5)—H and C(5)—H'), 3.73 (1H, m, C(3)—H), $^{13}$C NMR (75.46 MHz, $D_2O$) δ 13.16 ($PCH_3$, d, $J_{PC}$=91.6 Hz), 25.10 (C(5)), 31.31 (C(2)) 30.50 (C(4), d, $^3J_{PC}$=11.4 Hz), 37.34 (C(1), d, $J_{PC}$=98.2 Hz), 52.40 (C(3), d, $^3J_{PC}$=9.7 Hz), $^{31}$P NMR (121 MHz, $D_2O$) δ 45.9, MS (CI, $CH_4$) m/z 164 (38%) (MH$^+$), 147 (30), 105 (100), (ESI) 164.0821 (MH$^+$-$C_6H_{15}NO_2P$ requires 164.0840).

(±)-Isopropyl (3-aminocyclopentenyl)methylphosphinate (8)

To a solution of (±)-isopropyl (3-hydroxycyclopentenyl) methylphosphinate (3) (2.5 g, 12.25 mmol), DEAD (4.0 cm$^3$, 26.95 mmol) and $HN_3$ (12.9 cm$^3$ of a 1.9 M solution in benzene) in anhydrous THF (100 cm$^3$) at 0° C. was added triphenylphosphine (12.8 g, 49 mmol) in small portions over a period of 1 h. The reaction mixture was allowed to warm to room temperature and stirring continued for 12 h. The reaction mixture was then heated to 50° C. for 3 h after which time water (2 cm$^3$) was added and heating continued for a further 2 h. The reaction mixture was cooled to room temperature and the solvent removed in vacuo. The residue was partitioned between HCl (1M, 40 cm$^3$) and DCM (40 cm$^3$). The organic layer was separated and further extracted with water (3×30 cm$^3$). The combined aqueous fractions were washed with DCM (2×30 cm$^3$) and concentrated in vacuo. The crude product was purified by ion exchange chromatography (Dowex 50 H$^+$ form), eluting first with water until the eluate was neutral and then with aqueous ammonium hydroxide (1 M) collecting ninhydrin positive fractions. The solvent was removed in vacuo to yield the title compound as a pale yellow oil (8) (1.71 g, 68%): $^1$H NMR (300 MHz; $CD_3OD$) δ 1.26 and 1.27 (3H, d, J=6.0 and 6.0 Hz, $POCHCH_3$), 1.31 and 1.32 (3H, d, J=6.3 and 6.3 Hz, $POCHCH_3$), 1.51 and 1.53 (3H, d, J=14.4 and 14.1 Hz, $PCH_3$) 1.59–1.79 (1H, m, C(4)—H, 2.33–2.55 (2H, m, C(5)—H, C(5)—H'), 2.54–2.72 (1H, m, C(4)—H') 4.05 (1H, m, C(3)—H), 4.48 (1H, m, C(2)—H), 6.52 (1H, dm, J=9.9 Hz, PCCH), $^{13}$C NMR (75.46 MHz, $CD_3OD$) δ 13.92 and 14.10 ($PCH_3$, d, $J_{PC}$=102.1 and 101.6 Hz), 24.54 and 24.60 ($POCHCH_3$, 2×d, $^3J_{POCC}$=46 Hz), 24.9 ($POCHCH_3$, d, $^3J_{POCC}$=3.4 Hz), 32.86 and 32.88 (C(4), d, $^3J_{PC}$=12.6 and 12.3 Hz), 35.0 and 35.13 (C(5), 2×d, $^2J_{PC}$=10.0 Hz) 59.83 and 60.07 ($POCHCH_3$, d, $^2J_{POC}$=5.7 and 5.7 Hz), 71.36 and 71.39 (C(3), d, $^3J_{PC}$=6.3 and 6.3 Hz), 137.96 (C(1), d, $J_{PC}$=125.7 Hz), 150.84 and 150.95 (C(2), d, $^2J_{PC}$=10.9 and 11.1 Hz), $^{31}$P NMR (121 MHz, $CD_3OD$) δ 45.9, MS (EI) m/z 204 (38%) (MH$^+$), 147 (30), 105 (100) (ESI) 204.1151 (MH$^+$-$C_9H_{19}NO_2P$ requires 204.1153).

(±)-Isopropyl [3-(t-butyloxycarbonylamino)cyclopentenyl] methylphosphinate (9)

To a solution of (±)-isopropyl (3-aminocyclopentenyl) methylphosphinate (8) (1.5 g, 7.4 mmol) in aqueous sodium hydroxide (326 mg, 8.15 mmol in 25 cm$^3$) was added di-t-butyl dicarbonate (1.78 g, 8.15 mmol). The reaction mixture was stirred at room temperature for 16 h after which time the aqueous solution was extracted with DCM (4×30 cm$^3$). The crude product was purified by short column vacuum chromatography on silica gel (15% ethanol/ethyl acetate) to yield the desired product (9) as a colourless oil (2.1 g, 95%): $^1$H NMR (300 MHz, $CDCl_3$) δ 1.24 (3H, 2×d, J=6.3 Hz, $POCHCH_3$), 1.32 (3H, d, J=6.3 Hz, $POCHCH_3$), 1.44 (9H, br. s, $C(CH_3)_3$) 1.48 and 1.49 (3H, d, J=14.7 and 14.1 Hz, $PCH_3$) 1.58–1.75 (1H, m, C(4)—H), 2.41–2.72 (3H, m, C(5)—H, C(5)—H' and C(4)—H') 4.53 (2H, m, $POCHCH_3$ and $NHC(CH_3)_3$), 4.84 (1H, br. m, C(3)—H), 6.43 (1H, m, C(2)—H), $^{13}$C NMR (75.46 MHz, $CDCl_3$) δ 14.18 and 14.35 ($PCH_3$, d, $J_{PC}$=101 and 101 Hz), 24.09 and 24.14 ($POCHCH_3$, 2×d, $^3J_{POCC}$=3.9 Hz), 24.49 ($POCHCH_3$, d, $^3J_{POCC}$=3.4 Hz) 28.4 ($C(CH_3)_3$), 31.61 (C(4), d, $^3J_{PC}$=11.6 Hz), 32.45 and 32.52 (C(5), 2×d, $^2J_{PC}$=5.0 Hz), 57.64 and 57.87 (C(CH)$_3$, br. s), 69.26 ($POCHCH_3$, d, $^2J_{POC}$=6.4 Hz), 79.65 (C(3), br. s), 139.11 and 139.20 (C(1), d, $J_{PC}$=127.5 and 128.6 Hz), 145.0 (C(2), d, $^2J_{PC}$=11.3 Hz), 155.12 (C=O), $^{31}$P NMR (121 MHz, $CDCl_3$) δ 56.70, 56.75, MS (EI) m/z 304 (38%) (MH$^+$), 147 (30), 105 (100), (ESI) 304.1681 (MH$^+$-$C_{14}H_{26}NO_4P$ requires 304.1678).

(±)-cis-Isopropyl [3-(t-butyloxycarbonyl) aminocyclopentanyl]methylphosphinate (10)

A solution of isopropyl (3-t-butyloxyaminocyclopentenyl)methylphosphinate (9) (3.4 g, 10.7 mmol) in methanol (30 cm$^3$) was hydrogenated over platinum oxide (50 mg) at 40 psi for 3 h. The catalyst was removed by filtration through celite and then washed with methanol (3×30 cm$^3$). The solvent was removed in vacuo and the crude product was purified by short column vacuum chromatography on silica gel (15% ethanol/ethyl acetate) to yield the desired cis isomer (10) as a colourless oil (2.1 g, 95%): $^1$H NMR (300 MHz, $CDCl_3$) δ 1.24 (3H, 2×d, J=6.3 Hz, $POCHCH_3$), 1.32 (3H, d, J=6.3 Hz, $POCHCH_3$), 1.44 (9H, br. s, $C(CH_3)_3$), 1.48 and 1.49 (3H, d, J=14.7 and 14.1 Hz, $PCH_3$), 1.58–1.75 (2H, m, C(2)—H, C(4)—H), 2.41–2.72 (5H, m, C(1)—H, C(2)—H', C(4)—H', C(5)—H and C(5)—H'), 4.53 (2H, m, $POCHCH_3$ and NH), 4.84 (1H, br. m, C(3)—H), $^{13}$C NMR (75.46 MHz, $CDCl_3$) δ 12.78 and 12.96 (PCH3, d, $J_{PC}$=89.0 and 89.6 Hz), 23.58 (C(5)), 24.16 and 24.25 ($POCHCH_3$, d, $^3J_{POCC}$=3.4 and 3.9 Hz), 28.35 ($C(CH_3)_3$), 33.05 (C(2), s), 33.51 and 33.61 (C(4), 2×d, $3J_{PC}$=8.0 Hz), 35.85 and 35.93 (C(1), d, $J_{PC}$=100.2 and 100.1 Hz), 52.21 (C(CH)$_3$, br. s), 68.76 and 68.81 ($POCHCH_3$, d, $^2J_{POC}$=6.9 and 6.9 Hz), 79.2 (C(3), br. d, $^3J_{PC}$=5.0 Hz), 155.32 and 155.35 (C=O, s), $^{31}$P NMR (121 MHz, $CDCl_3$) δ 56.70, 56.75, MS (EI) m/z 277 (38%) (MH$^+$), 306 (30), (ESI) 306.1821 (MH$^+$-$C_{14}H_{28}NO_4P$ requires 306.1834).

(±)-cis-(3-Aminocyclopentanyl)methylphosphinic acid (11)

(±)-cis-Isopropyl [3-(t-butyloxyamino)cyclopentanyl] methylphosphinate (10) (2.1 g, 9.6 mmol) was dissolved in aqueous HCl (6M, 40 cm$^3$) and the solution heated at reflux for 30 h. After cooling, the solution was evaporated to dryness under reduced pressure. The residue was dissolved in water (10 cm³) and applied to an ion exchange column (Dowex 50, H⁺ form). The column was eluted with water until the eluate was colourless and pH neutral and then eluted with aqueous pyridine (1M). Ninhydrin positive fractions were combined and evaporated to dryness under reduced pressure. Residual traces of pyridine were removed by repeatedly redissolving the compound in water (20 cm³) and re-evaporating (3 times). Recrystallisation from ethanol/acetone and drying gave the title compound (11) as an off white solid (1 g, 46%): ¹H NMR (300 MHz, D₂O) δ 1.27 (3H, d, J=12.9 Hz, PCH₃), 1.56–2.27 (7H, m, C(1)—H, C(2)—H, C(2)—H', C(4)—H, C(4)—H', C(5)—H and C(5)—H), 3.59 (1H, m, C(3)—H), ¹³C NMR (75.46 MHz, D₂O) 13.02 (PCH₃, d, $J_{PC}$=92.0 Hz), 23.9 (C(5)), 30.50 (C(4), d, $^3J_{PC}$=7.5 Hz), 31.55 (C(2)), 37.20 (C(1), d, $J_{PC}$=97.3 Hz), 52.29 (C(3), d, $^3J_{PC}$=9.3 Hz), 31P NMR (121 MHz, D₂O) δ 45.9, MS (CI, CH₄) m/z 164 (38%) (MH⁺), 147 (30), 105 (100). (ESI) 164.0822 (MH⁺-C₆H₁₅NO₂P requires 164.0840).

Pharmacology

TPMPA ($K_B$=2.1 μM) is a selective $GABA_C$ receptor antagonist. It is 100-times more selective for $GABA_C$ than $GABA_A$ receptors and 500-times more selective for $GABA_C$ than $GABA_B$ receptors. TPMPA (300 μM) reduced the current produced by GABA (10 μM) by 67% at $GABA_A$ receptors while a dose of 500 μM was needed to produce about 30% activation of the $GABA_B$ receptor (Ragozzino et al, 1996).

In a similar manner to that described above for (±)-cis- and (±)-trans-3-ACPBPA, the activity of (±)-cis- and (±)-trans-3-ACPMPA as $GABA_C$ receptor antagonists and their selectivity as $GABA_C$ receptor antagonists was determined.

(±)-cis-($K_B$=1 μM) and (±)-trans-3-ACPMPA $K_B$=6.6 μM) are $GABA_C$ receptor antagonists. (±)-cis-3–3ACPMPA was shown to be 2-times more potent, while in contrast, (±)-trans-3-ACPMPA was 3-times less potent than TPMPA ($K_B$=2.1 μm). These compounds had very weak activity as antagonists at $GABA_A$ receptors. (±)-cis-(300 μM) and (±)-trans-3-ACPMPA (300 μM) reduced the current produced by GABA (10 μM) by 8% and 11% respectively. In contrast, (±)-cis-($EC_{50}$=50 μM) and (±)-trans-3-ACPMPA ($EC_{50}$=160 μM) were moderately potent $GABA_B$ receptor agonists.

These results indicate that (±)-cis- and (±)-trans-3-ACPMPA have a greater selectivity for $GABA_C$ compared to $GABA_A$ receptors, but have reduced selectivity for $GABA_C$ compared to $GABA_B$ receptors, relative to the selectivity of TPMPA. For example, (±)-cis-3-ACPMPA is more than 100-times more selective for $GABA_C$ than $GABA_A$ receptors but only 50-times more selective for $GABA_C$ than $GABA_B$ receptors. (±)-trans-3-ACPMPA is less selective than (±)-cis-3-ACPMPA being only 24-times more potent at $GABA_C$ than at $GABA_B$ receptors and 45-times more potent at $GABA_C$ than at $GABA_A$ receptors.

Comparison with (±)-cis- and (±)trans-3-ACPBPA

At the $GABA_A$ receptor, both (±)-cis- and (±)-trans-3-ACPBPA were shown to have no effect as an agonist or an antagonist even when tested at a 1 mM concentration. Similarly, (±)-cis- and (±)-trans-3-ACPBPA (300 μM) at $GABA_B$ receptors showed no effect as agonists or antagonists. Increasing the concentration to 1 mM only showed weak effects as antagonists (10% inhibition of 1 μM GABA) at this receptor. In contrast, (±)-cis- and (±)-trans-3-ACPBPA were shown to be potent antagonists at all $GABA_C$ receptor subtypes (ρ1, ρ2 and ρ3) indicating superior selectivity of (±)-cis- and (±)-trans-3-ACPBPA for $GABA_C$ over $GABA_B$ or $GABA_A$ receptors.

In comparison, (±)-cis-3-ACPMPA (the methyl analogue) is 12 times more potent than (±)-cis-3-ACPBPA at the $GABA_C$ receptors. However, (±)-cis-3-ACPMPA has reduced selectivity for $GABA_C$ over $GABA_B$ receptors, being only 50-times more selective for $GABA_C$ receptors. Therefore, (±)-cis-3-ACPBPA (the butyl analogue) has demonstrated to be a ligand with improved selectivity for the $GABA_C$ receptors being more than 100-times more selective for $GABA_C$ than either $GABA_A$ or $GABA_B$ receptors.

(±)-trans-3-ACPBPA, while weaker than (±)-cis-3-ACPBPA, shows similar selectivity for $GABA_C$ over $GABA_B$ receptors.

EXAMPLE 3

Synthesis of (±)-cis- and (±)-trans-(3-aminocyclopentanyl) propyl phosphinic acid.

(±)-Ethyl [3-(butoxycarbonyl)aminocyclopent-1-enyl] propylphosphinate was prepared in several steps by the method described in Example 1 for the synthesis of the butyl analogue: colourless/pale yellow oil; ¹H nmr (300 MHz, CDCl₃, referenced to internal TMS at δ 0.0 ppm) δ 1.02 (3H, m (as tm, J=7.1 Hz, CH₃), 1.31 and 1.32 (total 3H, 2×t, J=7.0 Hz, OCH₂CH₃ of diastereoisomers), 1.45 (9H, s), 1.53–1.80 (5H, m), 2.38–2.55 (2H, m), 2.55–2.69 (1H, m), 3.87–4.02 (1H, m, OCH), 4.01–4.16 (1H, m, OCH), 4.56 (1H, br d, J=7.9 Hz, NH), 4.86 (1H, m, CHNH), 6.48 (1H, dm, J=9.5 Hz); ¹³C nmr (75.45 MHz, CDCl₃, referenced to CDCl₃ at δ 77 ppm) δ 155.0 (C=O), 145.15 and 145.0 (2×d, J=3ca. 12.2 Hz, HC=C), 138.7 (d, J=119.4 Hz, PC=C), 79.6, 60.3 (d, J=6.3 Hz), 57.7(d, J=15.8 Hz), 32.4 (d, J=8.6 Hz), either {31.9 and 31.8 (2×d, J=2.6 Hz)} or {31.87 and 31.83 (2×d, J=8.6 Hz)}, 30.4 and 30.2 (2×d, J=99.3 Hz), 28.3 (C(CH₃)₃), 16.51 and 16.49 (2×d, J=6.2 Hz, OCH₂CH₃), 15.4 (d, J=16.3 Hz, PCH₂CH₂CH₃), 15.2 (d, J=3.7 Hz, PCH₂CH₂CH₃)

(±)-cis-Ethyl and (±)-trans-ethyl [3-(butoxycarbonyl)amino-cyclopentanyl]propylphosphinates A solution of ethyl (±)-[3-(t-butoxycarbonyl) aminocyclopent-1-enyl]propyl-phosphinate (1.04 g, 3.28 mmol) in MeOH (25 mL) was hydrogenated at 40 psi over PtO₂.H₂O (70 mg) until uptake ceased (ca. 18 h.). The mixture was allowed to settle and the clear solution carefully decanted from the catalyst (alternatively the catalyst may be removed by filtration through celite). The solvent was removed in vacuo to yield crude product as a colourless/pale yellow oil which partly crystallised (0.99 g, ratio of cis:trans products ca. 5:2). Separation by column chromatography (CC) (Silica Gel; EtOAc containing 1% EtOH initially, rising to 2% for complete elution of the second component) afforded (in order of elution):

(±)-cis-ethyl [3(butoxycarbonyl)aminocyclopentanyl] propylphosphinate as a low melting white solid (700 mg, 67%); 1H nmr (300 MHz, CDCl₃, referenced to internal TMS at δ 0.0 ppm) δ 1.03 (3H, t (actually 2×superimposed with very slightly different coupling constants), J=7.2 Hz, CH₃), 1.31 and 1.32 (total 3H, 2×t, J=7.0 Hz, OCH₂CH₃ of diastereoisomers), 1.43 (9H, s, C(CH₃)₃), 1.50–2.06 (9H, m), 2.08–2.28 (2H, m), 3.98–4.19 (3H, m, NCH and OCH₂), 5.40 and 5.59 (total 1H, 2×br d, J=6.2 Hz, NH of diastereoisomers); MS (CI, CH₄) m/z 348.1 H⁺+28,6%), 320 (MH⁺, ≤1%), 246.0 (24%), 220.1 (100%). and (±)-trans-ethyl [3-(butoxycarbonyl)amiocyclopentanyl] propyl-phosphinate as a low melting white solid (260 mg, 25%): ¹H nmr (300 MHz, CDCl₃, referenced to iternal TMS at δ 0.0 ppm) δ 1.02 (3H, t (actually 2×superimposed with very slightly different coupling constants), J=7.1 Hz, CH₃), 1.297 and 1.300 (total 3H, 2×t, J=7.0 Hz, OCH₂CH₃ of diastereoisomers), 1.44 (9H, s, C(CH₃)₃), 1.44–1.74 (5H, m), 1.74–2.00 (3H, m), 2.00–2.19 (2H, m), 2.18–2.36 (1H, m), 3.98–4.13 (3H, m, NCH and OCH$_2$), 4.47 (1H, br s, NH of diastereoisomers).

(±)-cis-(3-Aminocyclopentanyl)propylphosphinic acid (±)-cis-Ethyl [3-(butoxycarbonyl)aminocyclopentanyl] propylphosphinate (640 mg, 2 mmol) was deprotected (hydrolysed) according to the procedure described for the butyl analogue. Recrystallisation (EtOH/Acetone) of the crude product (380 mg) afforded product as white crystals (325 mg, 85%): $^1$H nmr (300 MHz, D$_2$O, referenced to DOH at δ 4.80 ppm) δ 0.93 (3H, t, J=ca. 7.0 Hz with some 2nd order effects, CH$_3$), 1.38–1.56 (4H, m), 1.62–1.97 (4H, m), 1.97–2.12 (1H, m), 2.22–2.30 (2H, m), 3.64–3.74 (1H, m, H$_2$NCH); $^{13}$C nmr (75.45 MHz, referenced to dioxan internal standard at 67 67.4 ppm) δ 16.1 (d, J=15.6 Hz, CH$_3$), 16.4 (d, J=3.8 Hz, PCH$_2$CH$_2$), 24.6 (C(5)H$_2$), 31.4 (d, J=7.1 Hz, C(4)H$_2$), 31.5 (d, J=91 Hz, PCH$_2$), 32.2 (C(2)H$_2$), 37.1 (d, J=93 Hz, CHP), 53.2 (d, J=8.4 Hz, CHN); MS (CI, CH$_4$) m/z 220.1 (MH$^+$+28, 27%), 192.1 (MH$^+$, 100%), 175.1 (23%), 174.1 (18%).

(±)-trans-(3-Aminocyclopentanyl)propylphosphinic acid (±)-trans-Ethyl [3-(butoxycarbonyl)aminocyclopentanyl] propylphosphinate (210 mg, 0.66 mmol) was deprotected (hydrolysed) according to the procedure described for the butyl analogue to afford product as a white powder (115 mg crude, ca. 92%): $^1$H nmr (300 MHz, D$_2$O, referenced to DOH at δ 4.80 ppm) δ 0.93 (3H, t, J=ca. 7.0 Hz with some 2nd order effects, CH$_3$), 1.38–1.52 (4H, m), 1.56–1.78 (2H, m), 1.78–1.92 (1H, m), 1.92–2.29 (4H, m), 3.65–3.75 (1H, m, H$_2$NCH); $^{13}$C nmr (75.45 MHz, D$_2$O, referenced to dioxan internal standard at δ 67.4 ppm) δ 16.1 (d, J=15.7 Hz, CH$_3$), 16.4 (d, J=3.7 Hz, PCH$_2$CH$_2$), 25.7 (C(5)H$_2$), 31.6 (d, J=91 Hz, PCH$_2$), 31.7 (C(2)H$_2$), 32.1 (d, J=9.4 Hz, C(4)H$_2$), 37.0 (d, J=95 Hz, CHP), 53.2 (d, J=9.5 Hz, CHN); MS (CI, CH$_4$) m/z 220.2 (MH$^+$+28, 57%), 192.1 (MH$^+$, 100%), 175.1 (50%).

EXAMPLE 4

Synthesis of (±)-cis- and (±)-trans-(3-aminocyclopentanyl) pentylphosphinic acid.

(±)-Ethyl [3-(1butoxycarbonyl)aminocyclopent $^1$-enyl] pentylphosphinate was prepared in several steps by the method described in Example-1 for the synthesis of the butyl analogue: colourless/pale yellow, viscous oil; 1H nmr (300 MHz, CDCl$_3$, referenced to internal TMS at δ 0.0 ppm) δ 0.89 (3H, m (as tm, J=7.1 Hz, CH$_3$), 1.28–1.4 (4H, m), 1.31 and 1.32 (total 3H, 2×t, J=7.0 Hz, OCH$_2$CH$_3$ of diastereoisomers), 1.45 (9H, s), 1.45–1.81 (5H, m), 2.38–2.55 (2H, m), 2.55–2.69 (1H, m), 3.87–4.16 (1H, m, OCH), 4.01–4.16 (1H, m, OCH), 4.58 (1H, br d, J=7.9 Hz, NH), 4.86 (1H, m, CHNH), 6.48 (1H, dm, J=9.5 Hz); $^{13}$C nmr (75.45 MHz, referenced to CDCl$_3$ at δ 77 ppm) δ 155.1 (C=O), 146.3 and 146.0 (2×d, J=ca. 10.6 Hz, HC=C), 138.6 (d, J=120 Hz, PC=C), 79.6, 60.3 (d, J=6.3 Hz), 57.7 (d, J=17.7 Hz), 32.9 (d, J=15.6 Hz), 32.42 and 32.41 (2×d, J=8.5 Hz), 31.91 and 31.86 (2×d, J=2.6 Hz), 28.3, C(CH$_3$)$_3$), 28.25 and 28.1 (2×d, J=99.6 Hz, PCH$_2$), 22.1, 21.1 (d, J=3.7 Hz, PCH$_2$CH$_2$CH$_2$),16.51 and 16.49 (2×d, J=6.3 Hz, OCH$_2$CH$_3$),13.8 (CH$_2$CH$_2$CH$_3$).

(±)-cis-Ethyl and (±)-trans-ethyl [3-(butoxycarbonyl)aminocyclopentanyl]pentylphosphinates A solution of ethyl (±)-[3-(t-butoxycarbonyl) aminocyclopent-1-enyl]pentylphosphinate (1.98 g, 5.73 mmol) in MeOH (40 mL) was hydrogenated at 40 psi over PtO$_2$.H$_2$O (70 mg) until uptake ceased (ca. 18 h.). The mixture was allowed to settle and the clear solution carefully decanted from the catalyst (alternatively the catalyst may be removed by filtration through celite). The solvent was removed in vacuo to yield crude product as a colourless/pale yellow oil (1.99 g, ratio of cis:trans products ca. 3:1). Separation by column chromatography (CC) (Silica Gel; EtOAc containing 1% EtOH initially, rising to 2% for complete elution of the second component) afforded (in order of elution): (±)-cis-ethyl [3-(butoxycarbonyl) aminocyclopentanyl]pentylphosphinate as a colourless oil (1.45 g, 73%); $^1$H nmr (300 MHz, CDCl$_3$, referenced to internal TMS at δ 0.0 ppm) δ 0.90 (3H, t, J=7.1 Hz, CH$_3$), 1.29–1.41 (4H, m), 1.317 and 1.323 (total 3H, 2×t, J=7.0 Hz, OCH$_2$CH$_3$ of diastereoisomers), 1.43 (9H, s, C(CH$_3$)$_3$), 1.43–2.07 (9H, m), 2.08–2.30 (2H, m), 3.98–4.19 (3H, m, OCH$_2$ and HNCH), 5.42 and 5.60 (total 1H, 2×d, J=7.7 Hz, NH); MS (CI, CH$_4$) m/z 376.2 (MH$^+$+28, 6%), 348.1 (MH$^+$, 10%), 274.1 (7%), 248.2 (100%). and (±)-trans-ethyl [$^3$-(butoxycarbonyl)aminocyclopentanyl] pentyl-phosphinate as a colourless oil (490 mg, 25%): 1H nmr (300 MHz, CDCl$_3$, referenced to internal TMS at δ 0.0 ppm) δ 0.90 (3H, t, J=7.1 Hz, CH$_3$), 1.300 and 1.305 (total 3H, 2×t, J=7.0 Hz, OCH$_2$CH$_3$ of diastereoisomers), 1.30–1.42 (4H, m), 1.44 (9H, s, C(CH$_3$)$_3$), 1.44–2.00(8H, m), 2.00–2.18 (2H, m), 2.18–2.36 (1H, m), 4.00–4.16 (3H, m, OCH$_2$ and HNCH), 4.50 (1H, m, NH);.MS (CI, CH$_4$) m/z 376.2 (MH$^+$+28, 15%),348.0 (MH$^+$, 8%), 320.2 (9%), 292.1 (100%).

(±)-cis-(3-Aminocyclopentanyl)pentylphosphinic acid (±)cis-Ethyl [3-(butoxycarbonyl)aminocyclopentanyl] pentylphosphinate (1.29 mg, 3.71 mmol) was deprotected (hydrolysed) according to the procedure described for the butyl analogue. Recrystallisation (EtOH/Acetone) of the crude product (780 mg) afforded product as white crystals (580 mg, 71%): $^1$H nmr (300 MHz, D$_2$O, referenced to DOH at δ 4.80 ppm) δ 0.84 (3H, t, J=7.1 Hz, CH$_3$), 1.21–1.36 (4H, m, 2×CH$_2$), 1.38–1.57 (4H, m, 2×CH$_2$),1.66–2.10 (5H, m), 2.11–2.30 (2H, m), 3.64–3.74 (1H, m, CNHM$_2$); $^{13}$C nmr (75.45 MHz, D$_2$O, referenced to dioxan internal standard at δ 67.4 ppm) δ 14.0 (CH$_3$),22.3 (d, J=4.0 Hz, PCH$_2$CH$_2$), 22.4 (PCH$_2$CH$_2$CH$_2$CH$_2$), 24.6 (C(5)H$_2$), 29.1 (d, J=91 Hz, PCH$_2$), 31.5 (d, J=7.0 Hz, C(4)H$_2$), 32.2 (C(2)H$_2$), 33.5 (d, J=14.8 Hz, PCH$_2$CH$_2$CH$_2$), 37.0 (d, J=93 Hz, CHP), 53.2 (d, J=8.6 Hz, CHN);.MS (CI, CH$_4$) m/z 248.1 (MH$^+$+28, 100%), 220.2 (MH$^+$, 27%), 202 (12%), 192 (4%):

(±)-trans-(3-Aminocyclopentanyl)pentylphosphinic acid (±)-trans-Ethyl [3-(butoxycarbonyl)aminocyclopentanyl] pentylphosphinate (450 mg, 1.3 mmol) was deprotected (hydrolysed) according to the procedure described for the butyl analogue to afford product as a white powder (270 mg crude, ca. 95%): 1H nmr (300 MHz, D$_2$O, referenced to DOH at δ 4.80, ppm) δ 0.84 (3H, t, J=7.2 Hz, CH$_3$), 1.20–1.37 (4H, m, 2×CH$_2$), 1.37–1.56 (4H, m, 2×CH$_2$), 1.56–1.76 (2H, m), 1.76–2.30 (5H, m), 3.66–3.76 (1H, m, CHNH$_2$);.$^{13}$C nmr (75 MHz, D$_2$O, referenced to dioxan internal standard at δ 67.4 ppm) δ 14.0 (CH$_3$), 22.2 (d, J=3.7 Hz, CH$_2$), 22.4 (CH$_2$), 25.7 (CH$_2$), 29.3 (d, J=91 Hz, PCH$_2$), 31.8 (CH$_2$), 32.1 (d, J=9.4 Hz, CH$_2$), 33.6 (d, J=14.9 Hz, CH$_2$), 36.9 (d, J=95 Hz, CHP), 53.1 (d, J=9.7 Hz, CHNH$_2$); .MS (CI, CH$_4$) m/z 248.1 (MH$^+$+28,40%), 220.0 (MH$^+$, 77%), 203.1 (100%), 202 (8%), 192 (4%).

EXAMPLE 5

General Behavioural and Acute Toxicity Tests

The overt behavioural effects and toxicity of (±)-cis- and (±)-trans-3-(aminocylopentanyl)butyl phosphinic acid in mice was examined. The overt behavioural effects of (±)-cis- and (±)-trans-3-(aminocylopentanyl)butyl phosphinic acid on mice after intraperitoneal injection were assessed using the protocol described in Irwin, 1996.

The compounds were tested at single doses of 1, 10 and 100 mg/kg administered by intraperitoneal injection. The compounds were administered in 10% propylene glycol in normal saline solution. Overt behavioural effects were observed for each animal at 0, 30 and 60 minutes, 24, 48 and 72 hours, and 1 week after injection. The cis-isomer produced no overt behavioural effects. The trans-isomer produced increased spontaneous activity, increase hypersensitivity and increased escape behaviour in some animals at doses of 10 and 100 mg/kg.

No overt acute toxicity was observed with either isomer.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

In the claims which follow and in the preceding description of the invention, except where the context requires otherwise due to express language or necessary implication, the word "comprising" or grammatical variations thereof, is used in the sense of "including", i.e. the features specified may be associated with further features in various embodiments of the invention.

References

Chebib M., Vandenberg R. J., Froestl W. and Johnston G. A. R. *Eur. J. Pharmacol.*, 1997 329, 223–229

Chebib M. *Chemistry in Australia*, October 2001, 19–21

Chebib M. and Johnston G. A. R. *J. Med. Chem.*, 2000 43, 1427–1447

Drew C. A., Johnston G. A. R. and Weatherby R. P. *Neurosci. Let.* 1984 52, 317–321

Feigenspan A. Wössle H. and Bormann J. *Nature*, 1993 361, 159–162

Froestl W., Mickel, S. J., von Sprecher, G., Diel. P. J., Hall, R. G., Maier, L., Strub, D., Melillo, V., Baumann, P. A., Bemasconi, R., Gentsch, C., Hauser, K., Jaekel, J., Karlsson, G., Klebs, K., Maitre, L., Marescaux, C., Pozza, M. F., Schmutz, M., Steinmann, M. W., Riezen, H., Vassout, A., Mondadori, C., Olpe, H-R., Waldmeier, P.C., and Bittiger, H. *J. Med. Chem.*, 1995, 38, 3313–3331.

Irwin, S. "Comprehensive Observational Assessment: 1a. A Systematic, Quantitative Procedure for Assessing the Behavioural and Physiologic State of the Mouse", *Psychopharmacologia*, 1968 13, 222–257

Johnston, G. A. R., Curtis, D. R., Beart, P. M., Game, C. J. A., McCulloch, R. M. and Twitchin, B. J. *Neurochem.*, 1975 24, 157–160

Johnston, G. A. R., Allan, R. D., Kennedy, S. M. E. and Twitchin, B. "GABA-Neurotransmitters", *Alfred Benzon Symposium* 12, Munksgaard, 1978, p 149–164.

Johnston, G. A. R. *Pharmacol. Ther.*, 1996 69, 173–198 ("Johnston, 1996a")

Johnston, G. A. R. *Trends Pharmacol. Sci.*, 1996 1, 319–323 ("Johnston, 1996b")

Kerr, D. I. B. and Ong, J. *Pharmacol. Ther.*, 1995 67 187–246

Murata, Y., Woodward, RM., Miledi, R. and Overman, L. E. *Bioorg. and Med. Chem. Lett.*, 1996 6, 2071–2076

Piers, E., Grierson, J. R., Lau, C. K. and Nagakura, I. *Can. J Chem.* 1982, 60, 210

Qian, H. and Dowling, J. E. *Nature*, 1993 361, 162–164

Ragozzino, D., Woodward, R. M., Murata, F., Eusebi, F., Overman, L. E. and Miledi, R. *Mol. Pharmacol.*, 1996 50 1024–1030

Woodward, R. M., Polenzani, L. and Miledi, R. *Mol. Pharmacol.*, 1993 43, 609–625

What is claimed is:

1. The compound 3-(aminocyclopentanyl) butylphosphinic acid of the formula I:

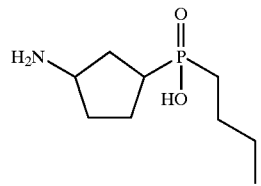

or a salt thereof.

2. A compound of the formula II

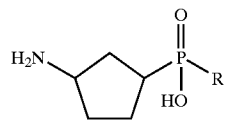

wherein R represents propyl, butyl, pentyl, neo-pentyl or cyclohexyl, or a salt thereof.

3. A compound according to claim 1 wherein the compound is in the cis-configuration.

4. A compound according to claim 1 wherein the compound is in the trans-configuration.

5. A method of selectively antagonising $GABA_C$ receptors compared to $GABA_B$ or $GABA_A$ receptors,.
    to enhance the cognitive activit of an animal, comprising:
        the step of exposing the receptors to an effective amount of the compund of formula II

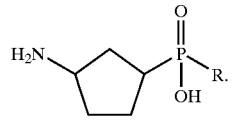

wherein R represents propyl, butyl, pentyl neo-pentyl or cyclohexyl, or a pharmaceutically acceptable salt thereof.

6. A method of enhancing the cognitive activity of an animal, comprising the step of administering to the animal an effective amount of a compound of formula II

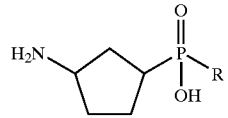

or a pharmaceutically acceptable salt thereof.

7. A method of stimulating memory capacity in an animal, comprising the step of administering to the animal an effective amount of a compound of formula II

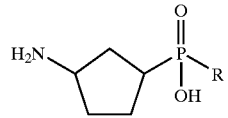

wherein R represents propyl, pentyl, neo-pentyl or cyclohexyl, or a pharmaceutically acceptable salt thereof.

8. A method according to claim 6 wherein the animal is suffering from a condition selected from the group consisting of cognitive deficit, memory impairment and dementia.

9. A method according to claim 6 wherein the animal is suffering from dementia, Alzheimer's disease, AIDS or schizophrenia.

10. A method according to claim 6 wherein the animal is a human.

11. A pharmaceutical composition comprising a compound of formula II

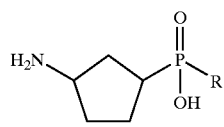

II wherein R represents propyl, butyl, pentyl, non-pentyl or cyclophexyl or a pharmaceutically acceptable salt thereof, and a pharmaceutically acceptable carrier.

12. A pharmaceutical composition according to claim 11 wherein R is butyl.

13. A compound according to claim 2 wherein the compound is in the cis-configuration.

14. A compound according to claim 2 wherein the compound is in the trans-configuration.

15. A method according to claim 5 wherein R is butyl.

16. A method according to claim 6 wherein R is butyl.

17. A method according to claim 7 wherein R is butyl.

* * * * *

UNITED STATES PATENT AND TRADEMARK OFFICE
CERTIFICATE OF CORRECTION

PATENT NO. : 6,962,907 B2
APPLICATION NO. : 10/496904
DATED : November 8, 2005
INVENTOR(S) : Mary Chebib, Jane Hanrahan and Graham A.R. Johnston It is certified that error appears in the above-identified patent and that said Letters Patent is hereby corrected as shown below:

Col. 38, line 28-29;
Claim 5, line 3, "...$GABA_A$ receptors,. to enhance the cognitive activity of an animal..." should read..--$GABA_A$ receptors to enhance the cognitive activity of an animal...--

Col. 38, line 39;
Claim 5, line 7, ..."Wherein R represents propyl, butyl, pentyl neo-pentyl..." should read....--Wherein R represents propyl, butyl, pentyl, neo-pentyl....--

Col. 38, line 52;
Claim 6, line 5,"...insert the following after structural formula II:
--wherein R represents propyl, butyl, pentyl, neo-pentyl or cyclohexyl...--

Col. 40, line 2;
Claim 11, line 5,"....replace "cyclophexyl" with --cyclohexyl--

Signed and Sealed this

Third Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 6,962,907 B2 Page 1 of 1
APPLICATION NO. : 10/496904
DATED : November 8, 2005
INVENTOR(S) : Chebib et al.

It is certified that error appears in the above-identified patent and that said Letters Patent is hereby corrected as shown below:

Item (73);
On the Title page of the patent, please change the Assignee to
    The University of Sydney, Sydney, Australia
    and
    Neuro Therapeutics Limited, Victoria, Australia Signed and Sealed this Twenty-third Day of December, 2008

JON W. DUDAS
*Director of the United States Patent and Trademark Office*